(12) United States Patent
Tajima et al.

(10) Patent No.: US 9,453,229 B2
(45) Date of Patent: *Sep. 27, 2016

(54) APPARATUS FOR INTRODUCING BIOLOGICAL MATERIAL, METHOD OF INTRODUCING BIOLOGICAL MATERIAL AND MAGNETIC SUPPORT FOR INTRODUCING BIOLOGICAL MATERIAL

(71) Applicants: UNIVERSAL BIO RESEARCH CO. LTD., Matsudo-shi, Chiba (JP); Yoshiro Okami, Ota-ku, Tokyo (JP)

(72) Inventors: Hideji Tajima, Chiba (JP); Yoshiro Okami, Tokyo (JP)

(73) Assignees: UNIVERSAL BIO RESEARCH CO. LTD., Matsudo-shi, Chiba (JP); Yoshiro Okami, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/050,272

(22) Filed: Oct. 9, 2013

(65) Prior Publication Data

US 2015/0004678 A1 Jan. 1, 2015

Related U.S. Application Data

(63) Continuation of application No. 10/531,520, filed as application No. PCT/JP03/13254 on Oct. 16, 2003, now Pat. No. 8,580,544.

(30) Foreign Application Priority Data

Oct. 16, 2002 (JP) .................................. 2002-301916

(51) Int. Cl.
   *C12N 13/00* (2006.01)
   *C12M 1/00* (2006.01)
   (Continued)

(52) U.S. Cl.
   CPC .............. *C12N 15/64* (2013.01); *C12M 35/02* (2013.01); *C12N 13/00* (2013.01); *C12N 15/87* (2013.01); *C12N 15/895* (2013.01); *Y10T 428/2982* (2015.01)

(58) Field of Classification Search
   CPC .................. B01L 3/502761; B01L 2400/043; B01L 2200/0647
   See application file for complete search history.

(56) References Cited

U.S. PATENT DOCUMENTS 3,985,649 A 10/1976 Eddelman
5,753,477 A 5/1998 Chan
(Continued)

FOREIGN PATENT DOCUMENTS

EP   866123 A1   9/1998
JP   58-179482 A   10/1983
(Continued)

OTHER PUBLICATIONS

Toneguzzo et al., "Electric field-mediated gene transfer: characerization of DNA transfer and patterns of integration on lymphoid cells," Nucleic Acid Research, 1988, vol. 16, No. 12, pp. 5515-5532.

Primary Examiner — Nathan Bowers
(74) Attorney, Agent, or Firm — Birch, Stewart, Kolasch & Birch, LLP

(57) ABSTRACT

The invention relates to an apparatus for introducing a biological material, a method of introducing a biological material, and a magnetic support for introducing a biological material with the object of providing an apparatus for introducing a biological material, a method of introducing a biological material, and a magnetic support for introducing a biological material whereby a biological material can be efficiently introduced into a host.

The invention comprises: one or more packing units in which a mixture solution containing a large number of magnetic supports carrying a biological material to be introduced into a host such as cells upon using, together with a large number of the hosts in a liquid is pooled; and an introduction treatment unit in which a magnetic force affecting the inside of the packing unit is controlled so as to move the magnetic supports relatively with respect to the host so that the biological material can be introduced into the host.

3 Claims, 14 Drawing Sheets

(51) Int. Cl.
*B01L 1/00* (2006.01)
*C12N 15/64* (2006.01)
*C12M 1/42* (2006.01)
*C12N 15/87* (2006.01)
*C12N 15/89* (2006.01)

(56) References Cited

U.S. PATENT DOCUMENTS

| | | |
|---|---|---|
| 6,281,008 B1 | 8/2001 | Komai et al. |
| 7,465,579 B2 | 12/2008 | Hatakeyama et al. |
| 2003/0044832 A1 | 3/2003 | Blankenstein |
| 2003/0073238 A1 | 4/2003 | Dzekunov et al. |
| 2003/0096220 A1 | 5/2003 | Lafferty et al. |

FOREIGN PATENT DOCUMENTS

| | | |
|---|---|---|
| JP | 6-133784 A | 5/1994 |
| JP | 7-241192 A | 9/1995 |
| WO | WO 94/09145 A1 | 4/1994 |
| WO | WO 97/31105 A1 | 8/1997 |
| WO | WO 99/42832 A1 | 8/1999 |
| WO | WO 01/55294 A1 | 8/2001 |

FIG. 3
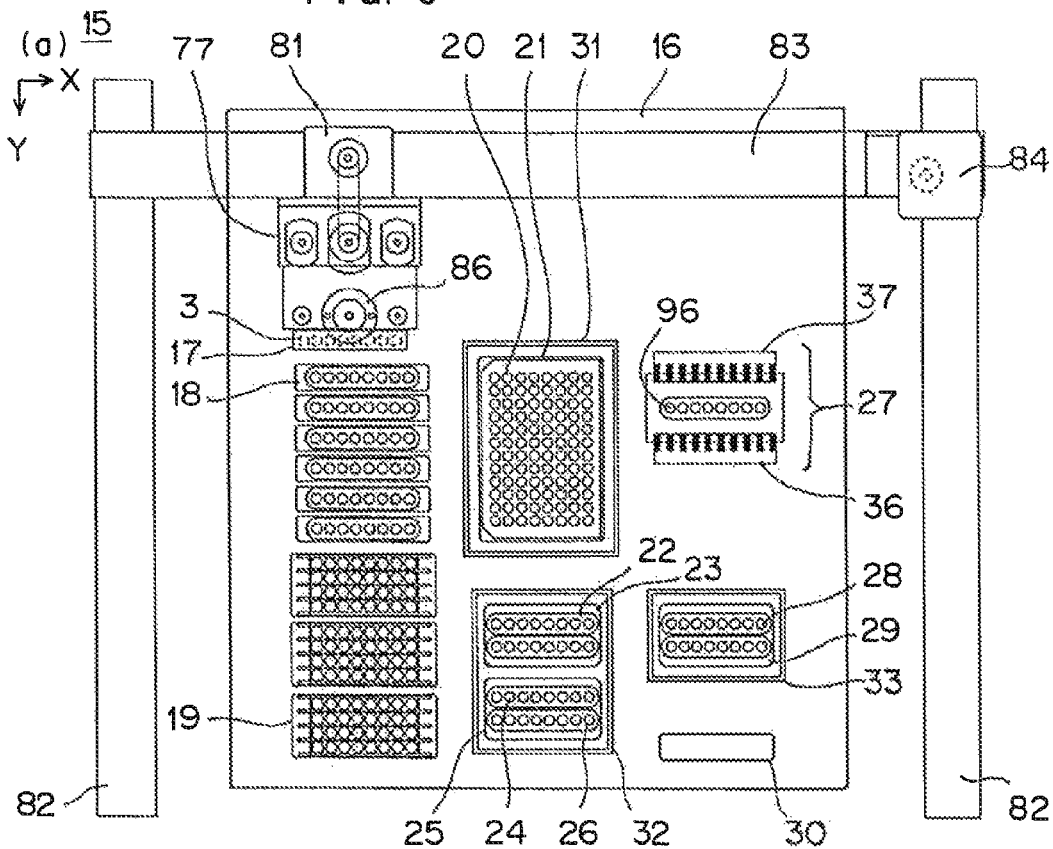
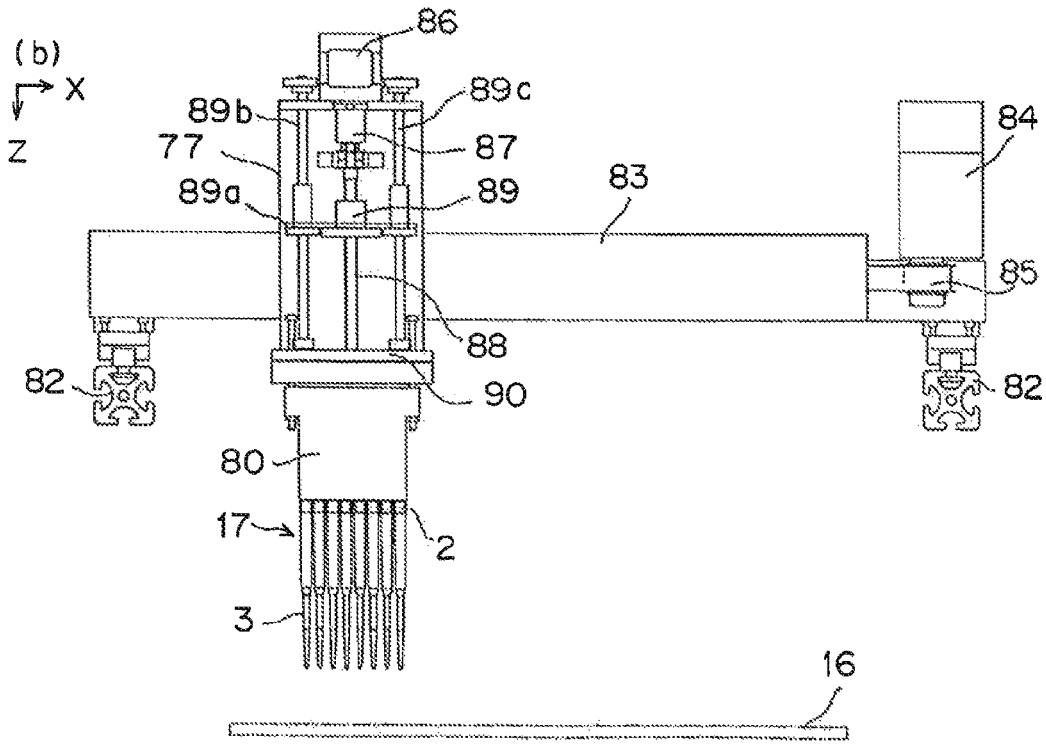

FIG. 15
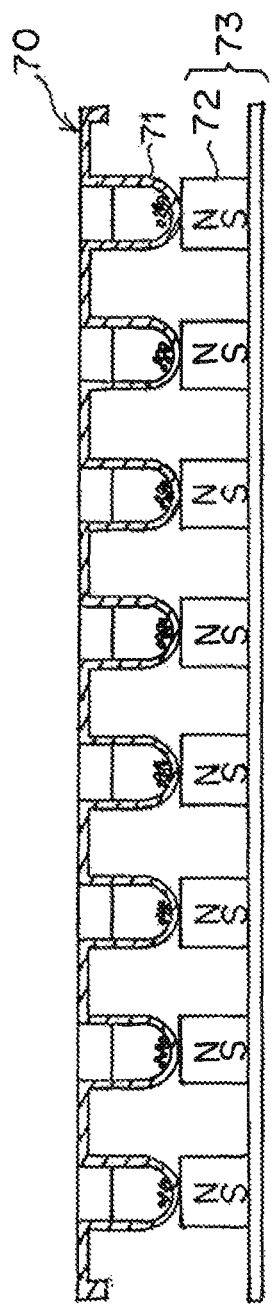
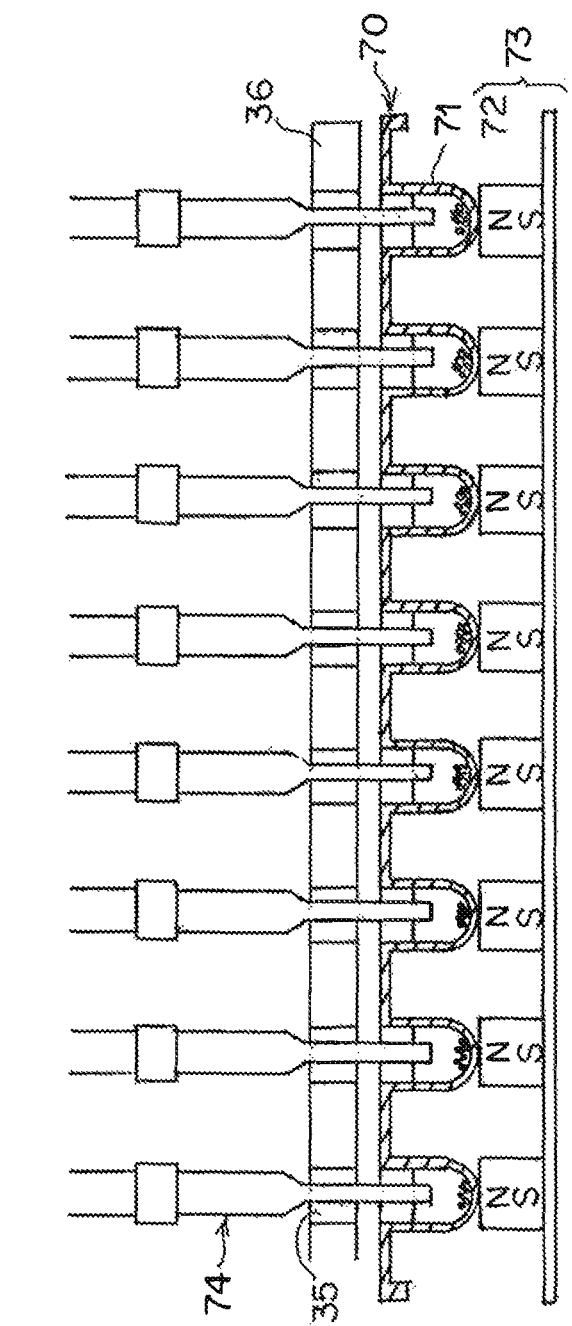

APPARATUS FOR INTRODUCING BIOLOGICAL MATERIAL, METHOD OF INTRODUCING BIOLOGICAL MATERIAL AND MAGNETIC SUPPORT FOR INTRODUCING BIOLOGICAL MATERIAL

This application is a Continuation of copending application Ser. No. 10/531,520 filed on Nov. 16, 2005, which is the National Stage Entry of PCT/JP2003/013254 filed on Oct. 16, 2003, which claims priority to Application No. 2002-301916 filed in Japan on Oct. 16, 2002. The entire contents of all of the above applications is hereby incorporated by reference.

TECHNICAL FIELD

The present invention relates to an apparatus for introducing a biological material, a method of introducing a biological material, and a magnetic support for introducing a biological material. Specifically, the invention relates to an apparatus for introducing a biological material, a method of introducing a biological material and a magnetic support for introducing a biological material by which a genetic material such as a foreign DNA can be introduced into a cell of an organism or a bacterium using a magnetic support, so as to be utilized in the various fields such as the manufacturing industry medical health care services, the pharmaceutical industry, apiculture, fishery, livestock industry, and biochemistry which perform DNA cloning, gene therapy, breeding of plants or animals, production of useful proteins, and biochemical analysis.

BACKGROUND ART

Conventionally, in the field of genetic engineering, in order to perform DNA cloning, gene therapy, or breeding, a vector is necessary as a carrier which brings a foreign target gene into a cell of an organism, in addition to enzymes which cut and paste genes. If a bacterium such as *E. coli* as a host is used as such a vector, a plasmid or a λ phage has been used and mixed with *E. coli* and the like, then electroshocked to introduce this. Moreover, in order to separate the *E. colis* introduced in this manner, the process has been such that, after a series of treatments to combine an antibiotic resistant gene resistant to antibiotics into the plasmid or the like, only cells which are transformed through the antibiotic treatment are extracted.

Moreover, there have been three methods for bringing a foreign target gene into an animal cell, namely; (1) to introduce a foreign gene as is (2) to introduce it by microinjection, and (3) to make a ret early it.

Introducing a foreign target gene as is, into an animal cell is performed by mixing calcium phosphate with the foreign genes, and then mixing the precipitated genes with the animal cells. The reason for this is that by so doing even a small number of cells can take-in the precipitated genes.

In the microinjection, a foreign gene is directly inserted into a cell nucleus using a micropipette (extra fine capillary tube) which is made from very fine glass having a diameter of 0.1 μm, while watching through a microscope.

Moreover, in older to use a retrovirus as a vector, a foreign target gene is sandwiched between the opposite terminals by a retrovirus LTR (transcriptional promoter and poly A-binding site) to create the vector, which is then introduced into an animal cell.

Furthermore, there is another method wherein the biological material is introduced using magnetic particles by shooting the magnetic particles fixed with the biological materials into cells, organs, or tissues at high speed (initial velocity is 50 to 400 m/second) (for example, refer to Japanese Unexamined Patent Publication No. 6-133784, paras. 14, 19, and 20). This method is to facilitate the concentration or separation of cells by using magnetic three.

Incidentally, in the conventional method of introducing a target gene described above, a parasitic genetic factor (extrachromosomal gene of a bacterium which can proliferate independently from chromosomes and the like) such as a plasmid or a virus such as a λ phage has been used as a vector. There has been a problem in that, the parasitic genetic factor and the virus are intrinsically pathogenic in many cases, and even if the pathogenicity is put out of action in use, they may recover the pathogenicity by recombining with another pathogen infected to the host. Moreover, there has been another problem in that, even if electroshock is applied during the introduction, the introduction efficiency is not high enough. Furthermore there has been another problem in that, due to the presence of the antibiotic resistant gene used when the introduced cells are extracted, the diffusion of the antibiotic resistant gene may negatively affect the environment of the host.

If the host is an animal cell, the first method can be readily performed since the operating procedure is simple. However, this method has a problem of extremely poor efficiency. The second method allows introducing the target gene into the cell nucleus reliably. However, there has been a problem in that to master this technique requires a reasonable technical training and takes time.

In the third method, a package cell strain having the autonomous replication-competence deleted and genes required for proliferation combined into a chromosome is used for ensuring the safety of the retrovirus. However, there has been a problem in that, similarly to the abovementioned plasmid, the retrovirus may recover the pathogenicity by recombining with another pathogen infected to the host.

In the method of shooting the magnetic particles fixed with the biological materials into cells at high speed using a firing apparatus, there have been problems in that the scale of the apparatus becomes larger, and that the magnetic particles which are once fired and go astray from the cells can not be reused, and hence the efficacy is low after all. Them has been another problem in that since they are shot at high speed, cells having low strength are broken down when the particles collide with the cells, making it impossible to introduce the biological materials thereinto.

As described above, any method has a problem of poor efficacy, since the way to introduce a biological material into a host is to let the host and the biological material suspended or contained in the solution encounter naturally, or to introduce the biological material into the host one by one manually, or only once by a firing apparatus.

Therefore, the present invention has been developed to solve the abovementioned problems, with a first object of providing an apparatus for introducing a biological material, a method of introducing a biological material, and a magnetic support for introducing a biological material, whereby a foreign biological material can be introduced into a host efficiently, not by relying on a natural encounter of a host and a biological material, but by using a magnetic force and controlling its magnitude, direction, location, and the like, to promote the collision by moving the magnetic support until it enters the host, or to promote the encounter by densifying the biological material in the solution.

A second object is to provide an apparatus for introducing a biological material, a method of introducing a biological material, and a magnetic support for introducing a biological material, wherein various treatments are standardized and automatically performed without relying on manpower nor skilled technicians, so that the introduction into a host can be readily performed.

A third object is to provide an apparatus for introducing a biological material, a method of introducing a biological material, and a magnetic support for introducing a biological material, whereby the introduction can be performed without using a recombinant of a virus or a parasitic genetic factor such as a plasmid, and a biological material can be introduced safely.

A fourth object is to provide an apparatus for introducing a biological material, a method of introducing a biological material, and a magnetic support for introducing a biological material, whereby a host having a foreign biological material introduced thereinto can be readily and reliably separated and extracted.

A fifth object is to provide an apparatus for introducing a biological material, a method of introducing a biological material, and a magnetic support for introducing a biological material, whereby the effect on the environment caused by combining an antibiotic resistant gene ma be avoided, enabling safe separation and extraction.

A sixth object is to provide an apparatus for introducing a biological material, a method of introducing a biological material, and a magnetic support for introducing a biological material, winch has variety and generality allowing introduction under various conditions according to the properties of hosts and biological materials.

DISCLOSURE OF THE INVENTION

In order to solve the abovementioned technical problems, a first aspect of the present invention provides an apparatus for introducing a biological material which has: one or more packing units in which a mixture solution containing a large number of magnetic supports carrying a biological material to be introduced into a host such as cells upon using, together with a large number of the hosts in solution is pooled; and an introduction treatment unit which controls a magnetic force affecting the inside of the packing unit so as to move the magnetic supports relatively with respect to the host in solution to introduce the biological material into the host.

"Host" means an object into which the foreign biological material is introduced, or is to be introduced, corresponding to for example, eukaryotic cells such as plant or animal cells (including human cell), prokaryotic cells such as bacteria, proteins, and the like.

"Biological material" is a material for giving desired properties to the host, and includes for example, genes, enzymes, antigens, antibodies, proteins, pheromones, allomones, mitochondria, viruses, plasmid, and the like.

The magnetic support carries the biological material by for example, physical adsorption, electrical interaction, chemical absorption, covalent binding, or the like.

"Magnetic support" is a support which is magnetic due to overall or partial magnetization, or which is magnetizable. Its properties such as shape, size, and susceptibility, and the amount, and density re determined by the method of introducing a biological material, and the properties, the amount, and the density of the host, and the like. The material of the magnetic support is for example a superparamagnetic single-domain particle having a surface stabilizing substance. The particle is made of for example, an iron hydroxide, an iron oxide hydrate, an iron oxide, a mixed iron oxide, or iron.

The size of the magnetic support is determined by conditions such as the type or the size of the host, or the type or the size of the biological material. For example, if the host is a prokaryotic cell, it would be about between 100 nm and 200 nm. If it is a eukaryotic cell such as for example, yeast or an animal cell, it would be between 1 μm and 2 μm.

If the biological material is introduced by adhering the magnetic support to the host, the shape of the magnetic support is globular for example, and the particle surface coating substance is required to be a material which has a good adhesion onto the surface of the host. Furthermore, in the case where the host can not be adhered, the cell membrane of the host is strong, or there is a cell wall, or in the case where the introduction into the host is performed without performing cell surface treatment, the magnetic support preferably has a shape with tapered ends.

"To control the magnetic force affecting the inside of the packing unit" means to control the direction or the size of a predetermined magnetic force affecting the inside of the packing unit, the relative position of the magnetic source with respect to the packing unit or the solution the relative speed or the acceleration of the magnetic source with respect to the packing unit or the solution, or the time to apply the magnetic force, so as to relatively move between the host and the magnetic support, to promote collision, thereby increasing the number of collisions or the rate of collision (average number of collisions per unit time), or for example, so as to move the magnetic support carrying the biological material with respect to a perforated host or a host which has a soft boundary not requiring migration treatment, to make an area where the biological material is densified mom than the surroundings, thus increasing the chance of encounter with the host, and enabling to increase the introduction efficiency.

In order to promote collisions or encounters, the relative movement distance of the magnetic support with respect to the host or the solution is preferably longer. For example, reciprocating rectilinear motion, rotation, vibration, or movement in a combination thereof, or periodic movement such as movement along other closed curves, or aperiodic repetitive movement, are preferable.

For this purpose, the magnetic three is applied not only from one direction, but also from at least two directions with the packing unit therebetween, and the magnitude, the direction, or the position thereof can be preferably controlled independently. The reason for this is such that, if the magnetic force is applied only from one direction, the magnetic supports are moved only in one direction and applied with the magnetic fare for a very short time, and then they are collided with the wall of the packing unit along the direction, coming into a state where they are attached to or aggregated on the wall. Once the magnetic supports come into a state where they are attached to or aggregated on the wall, the magnetic supports can not be released from the attachment state simply by removing the magnetic force. In such a state, it is difficult to promote collisions or encounters with the hosts which are widely scattered in solution or are aggregated in a part of the solution. In order to separate the magnetic supports in the attachment state to increase the chance of collision or encounter with the host in the solution, the magnetic force is applied in a direction to release the attached magnetic supports, for example in the opposite direction with the packing unit therebetween, against the direction of the magnetic force which makes the magnetic supports become attached, thereby enabling the magnetic supports to pass through the approximate center of the packing unit and be moved in the opposite direction. The chance of collision or encounter with the host is increased by repeating the above procedure. At this time, there where the magnetic force is applied from another direction after removing the magnetic force which makes the magnetic supports become attached, or where a magnetic force is added without removing the magnetic force.

Moreover, it is also possible to initially avoid or reduce the attachment of the magnetic supports onto the Wall of the packing unit so as to increase the chance of collision or encounter. For example, before the magnetic supports are attached onto the wall of the packing unit due to the magnetic force applied from one direction, they are reciprocated by applying a magnetic force from a different direction from the above direction. Furthermore, for example, magnetic forces having similar strengths are horizontally applied from at least two directions at the same time so that the combined magnetic forces applied to the magnetic support counterbalance each other or are reduced as little as possible, in the horizontal plane. Then, in the state where the magnetic supports are developed in the solution, the position where the magnetic force is applied is vertically reciprocated or rotated at the same time, so that the magnetic supports are vertically reciprocated or rotated.

By controlling as above, the chance of collision or encounter between the magnetic supports and the host can be increased more efficiently.

In this manner by moving the magnetic supports relatively with respect to the host in the solution by the magnetic force; by moving the magnetic supports relatively with respect to the host by releasing the magnetic supports from the attachment state by the magnetic force if they are attached onto the packing unit; by moving the magnetic supports relatively with respect to the host by initially avoiding a condition where the magnetic supports are aggregated due to the attachment caused by the collision with the packing unit; or by moving the magnetic supports relatively with respect to the host in a state where the magnetic supports are actively developed in the solution, the chance of collision or encounter between the magnetic supports and the host suspended in the solution can be increased.

Here, "two directions" mean the directions orientation into consideration. If the orientation is different the direction is also different "Apply the magnetic force from at least two directions with the packing unit therebetween" does not only mean a case where two directions are facing linearly with the packing unit therebetween, but also includes a case where they are facing at a certain angle with the packing unit therebetween. Moreover, it does not only mean a case where the combined magnetic foxes applied to the respective magnetic supports counteract each other, but also includes a case where the combined magnetic force is limited. Furthermore, it does not only mean a case where the magnetic forces in the respective directions are applied at the same time, but also includes a case where they are applied at different times. The magnitudes of the magnetic fortes in the respective directions are not limited to be the same. Since the magnetic force is applied to the packing unit, the direction of the magnetic force is oriented to pass through the inside of the packing unit. The magnetic forces in the respective directions are preferably related so as to control the magnitude, the direction, and the position. The magnetic forces are preferably controlled to be applied to the packing unit from many directions, so that the magnetic supports are moved around or distributed to develop in the solution.

The encounter of the magnetic support and the host means that the magnetic support and the host are in contact without perforating the host. Accordingly, the magnetic support is adhered to the host, or the magnetic support is made to enter the host. On the other hand, the collision of the magnetic support with the host means that the magnetic support and the host are in contact with perforation of the host. Accordingly, the magnetic support is adhered to the host or entered into the host with perforation. Therefore, in the introduction of the biological material by the encounter, depending on the property of the host, it is preferable to facilitate the introduction of the biological material by electroporation or the like, that is, to have the function of perforating the host. The packing unit is preferably formed of for example a glass, or a plastic such as polyethylene, polypropylene, or acrylic resins, being transparent or semitransparent.

In order to promote the encounter, for example, the magnetic supports are aggregated in a certain area in the solution in the direction of the magnetic force, to densify the area with more biological materials than the other areas. Such densification is effective in the case of a perforated host, or the case where the magnetic support enters a host for which perforation is not required for the magnetic support to enter according to its property.

According to the first aspect of the invention, by using the magnetic supports, the biological material can be mechanically or physically introduced without using a vector such as a virus by using the magnetic supports, so that the biological material can be introduced safely. Between the magnetic supports caning the biological material and the host in solution is relatively moved, not by relying on a natural encounter or collision with the host, but by controlling the magnetic force, to increase the number of collision or the rate of collision between the magnetic supports and the host, or to increase the chance of encounter with the host, so that the introduction of the biological material into the host can be promoted. Moreover, by using the magnetic supports having rigidity and mass, the impelling force is increased and movement is facilitated in the solution, more than when using the biological material only, so that the chance of collision or encounter with the host is increased, facilitating the introduction into the host.

Moreover, since the introduction is performed by controlling the magnetic form, then by optimizing the manner of collision such as the magnitude, the velocity, and the acceleration due to the magnetic force according to the properties of the host or the biological material, the host can be kept from being broken down, and a highly densified area of the magnetic supports can be made, or the magnetic supports are freely moved to the highly densified area of the host, so as to increase the chance of encounter. Moreover by combining in the above manners of collision, introduction having generality, variety, certainty, reliability, and efficiency can be performed.

A second aspect of the present invention is an apparatus for introducing a biological material, wherein the introduction treatment unit has: a magnetic source which can apply a magnetic force to the inside of the packing unit; and a magnetic force control unit which controls the magnetic supports to move relatively with respect to the host, by changing the relative position or the velocity between the packing unit or the mixture solution and the magnetic source, or the magnetic force itself due to the magnetic source.

Since the movement is "relative", the magnetic supports are relatively moved with respect to the host such that: the host or the mixture solution containing the host is made static or approximately static and the magnetic support is moved; the magnetic support is made static or approximately static and the mixture solution containing the host is moved; or the mixture solution containing the host and the magnetic support are both moved in different manners. If the host is a biological material such as a cell with low strength, the magnetic support is preferably moved. In order to avoid or reduce the collision of the magnetic supports onto the packing unit, the magnetic force is applied from at least two directions with the packing unit therebetween. Since "the position or the velocity is changed", uniform motion, accelerated motion, oscillation, rotation, and the like are included. "Velocity" is not only the magnitude of the speed but includes its direction.

The magnetic source is permanent magnets or electromagnets movably arranged around the packing unit, or fixed electromagnets arranged around the packing unit. The magnetic force control unit is a magnetic three transfer unit which relatively moves the magnetic source with respect to the packing unit, or a magnetic force modification unit which modifies the magnitude of the magnetic force of the electromagnet. The magnetic force transfer unit is for example: to move the magnetic source in the circumferential lateral surface direction of the packing unit or the vertical direction (including oscillation; the same applies hereunder); to move the magnetic source enabling it to come closer or go away with respect to the packing unit, or to vertically move, rotate, or horizontally move the packing unit relatively with respect to the magnetic source. Combinations of modification of the magnetic force and the movement of the position of the magnetic source allows various treatments to be performed on the magnetic supports.

According to the second aspect of the present invention, by providing a magnetic source which can modify the relative position or velocity between the packing unit or the mixture solution, and the magnetic source, or the magnetic force itself the magnetic support and the host are controlled to move relatively therebetween, so as to increase the number of collision or the rate of collision between the magnetic supports and the host, to densify the magnetic support, or to combine them both, enabling promotion of the introduction of the biological material. At this time, the magnetic forces of the magnetic sources are applied from at least two outside directions with the packing unit therebetween so that the combined magnetic force applied to the magnetic support counteract each other to avoid being unidirectionally biased against gravity, and the time is extended until the magnetic supports are attached to the wall. In this case, for example, when magnetic forces having similar strengths are horizontally applied in the facing directions with the packing unit therebetween, the magnetic support layer can be obtained. Furthermore, by changing the position of the magnetic source or the packing unit along the circumferential direction, the magnetic support layer is extended evenly. If the layer is vertically moved in this state, the number of collisions, the rate of collisions, or the chance of encounters can be increased.

A third aspect of the present invention is an apparatus for introducing a biological material wherein the introduction treatment unit moves the magnetic supports and the host relatively to each other in a state where a large number of the magnetic supports in the solution contained in the packing unit are developed by the magnetic force.

Here, "a state where a large number of magnetic supports are developed by the magnetic force the solution" means a state where a large number of the magnetic supports are spread and distributed in a certain area in the solution by receiving the magnetic force. This developed state includes a planar case and a three dimensional case, and is determined according to the distribution state of the host. The magnetic supports in the developed state are in suspension unless the magnetic force is moved. The magnetic support can be readily moved by moving the magnetic force.

For example, in the state where the host is widely scattered in the solution, the large number of magnetic supports are preferably developed in a planar form for being densified more than the surroundings so as to partition the packing uric and are controlled so as to move them in the normal direction of the developed surface. Moreover, if the host is aggregated in a partial area, the large number of magnetic supports are developed in the solution so as to have the cross-section covering the area, and are moved towards the direction of the area in the normal direction of the developed surface. In this manner, in a state where the large number of the magnetic supports are developed in the solution according to the distribution state of the host, the magnetic supports are moved in a direction to increase the chance of collision or encounter with the host along the normal direction of the developed surface of the magnetic supports.

Here, in order to realize the "developed state by the magnetic force", it is necessary to apply the magnetic force from at least two directions with the packing unit therebetween.

The third aspect of the present invention is to increase the number of collision or the rate of collision, or to increase the chance of encounter of the magnetic support, by making relative movement between the magnetic supports and the host in a state where the magnetic supports are developed in the solution in the packing unit. Therefore, attachment due to the collision with the packing unit is avoided, and the magnetic support layer is formed. Hence the number of collisions, the rate of collisions, or the chance of encounter with the magnetic support can be increased more widely.

A fourth aspect of the present invention is an apparatus for introducing a biological material wherein the magnetic support is a particle having a major axis and a size allowing entry into the host along a major axis direction.

Here, the magnetic support is preferably magnetized or magnetizable along the major axis direction. Accordingly the magnetic support can be readily controlled since it can be moved along the direction of the magnetic force. Moreover, if the magnetic support has a rotationally symmetric axis along the major axis direction, it can be readily controlled, since it can travel accurately in the intended direction by spinning it according to how the magnetic support travels.

In the fourth aspect of the present invention, the magnetic support has a major axis longer than the other axis and a size allowing entry into the host along the major axis direction, and can carry the biological material. Therefore it readily enters the host.

A fifth aspect of the present invention is an apparatus for introducing a biological material wherein an introduction adjuvant for helping to introduce the biological material into the host is contained in the packing unit together with the biological material. Here, "introduction adjuvant" includes for example: a calcium chloride which increases the cell membrane fluidity when a bacterial gene is introduced so as to facilitate the taking in of the plasmid, PEG (polyethylene glycol) which protoplastizes the animal cell membrane; chitinase which dissolves the cell wall; and an aggregation accelerant which promotes the aggregation of the hosts themselves since the introduction is promoted by increasing the chance of contact with the host. The aggregation accelerant includes for example a bivalent metal ion and the like which forms crosslinks between cells.

In the fifth aspect of the present invention, the introduction adjuvant for helping to introduce the biological material into the host is contained in the packing unit together with the biological material. Accordingly, by facilitating the host to take in the biological material, or by increasing the chance of contact of the magnetic support with the host, the introduction efficiency can be increased.

A sixth aspect to the present invention is an apparatus for introducing a biological material wherein the magnetic support has a carrier for caning the biological material.

Here, the carrier expands the area to contact with the biological material or the introduction adjuvant, enabling it to carry the biological material in a readily separable manner when the magnetic support enters the host, or comes into contact with or is adhered to the host by physical adsorption, electrical interaction, or the like. For example, it includes concavities, perforations, or gaps provided in the magnetic support itself, or other material or a support which is fixed or bonded to the magnetic support. An example of the concavities includes an annular groove provided along the circumference of the approximate center on the side face of the magnetic support. An example of perforations includes a magnetic material carrying a porous material by coating or the like if the magnetic material itself is processed, or a porous gel materials such as a cellulose gel, hydroxy-apatite, and the like caning the magnetic material and/or the biological material. The carrier may be provided inside of the magnetic support.

An example of other material or a support which is fixed or bonded to the magnetic support includes one or more filamentary supports. The biological material is carried by the filamentary supports. The filamentary supports are used, for example in a case where the host is not strong, such as a case where the cell membrane is weak, requiring introduction under a mild condition, in a case of a dilute fungus liquid, or in a case where handling is facilitated if they are aggregated. In this case, the respective filamentary supports are not introduced into the host, but a load is applied to the hosts entwined with the filamentary supports by controlling by a magnet, so that the force is applied as a line, and not as a point, to reduce damage. Since this case does not require processing of the magnetic support directly, manufacture is facilitated.

Moreover, a composite particle having a plurality of magnetic particles connected may be used as the magnetic support. A gap or necking of the junction between magnetic particles may be used as the carrier.

In the sixth aspect of the present invention, by providing the carrier for the magnetic support, the capacity of carrying the biological material and the like can be increased and the introduction can be reliably performed.

A seventh aspect of the present invention is an apparatus for introducing a biological material wherein in the magnetic support, both ends or one end along the major axis are formed in a tapered shape. Accordingly, the magnetic support can readily enter the host. In the seventh aspect of the present invention, the opposite ends or one end along the major axis of the magnetic support are formed in the tapered shape. Therefore, it is possible to facilitate entry into the host such as a cell having a hard cell wall or a cell membrane which is not surface treated by the introduction adjuvant, and to enter reliably.

An eighth aspect of the present invention is an apparatus for introducing a biological material wherein the introduction treatment unit performs introduction control based on the properties, the amount, or the density of the host, the biological material, or the magnetic support.

Here, the properties include physical properties, biological properties, and chemical properties. The physical properties include for example, strength, size, shape, mass, susceptibility, and the like. The biological properties include environmental conditions such as optimum temperature and the like. The chemical properties include properties of the host or the biological material with respect to acid or alkali, and toxicity with respect to metals, and the like. Whether or not the magnetic support readily enters by surface treatment, is included in the physical properties. For example, the momentum of the magnetic support to collide with the host is reduced with respect to a host having low strength, so as to avoid breaking down the host due to collision or encounter with each other. Moreover, with respect to a host having strength such as a plant cell with a cell wall, the momentum of the magnetic support to be collided with the host is increased to apply a force to pierce the cell wall. These data on the properties, the amount, and the density are input into an input device provided for the apparatus, so as to process them through an information processor which is connected to the apparatus for introducing a biological material, and thereby control the magnetic force including the optimum magnetic source.

In the eighth aspect of the present invention, since the introduction is controlled based on the properties, the amount, or the density of the host, the biological material, or the magnetic support, introduction treatment having variety and generality can be performed in an optimum way for various hosts and various biological materials.

A ninth aspect of the present invention is an apparatus for introducing a biological material wherein the packing unit has a liquid passage through which the mixture solution can pass, and has a pressure adjuster which draws and discharges the solution by adjusting the pressure in the liquid passage, as the magnetic force control unit.

Here, a storage unit which can stole, the solution may be provided on the packing unit in addition to the liquid passage. The liquid passage or the whole of the packing unit may be detachably attached to the nozzle of the pressure adjuster.

In the apparatus for introducing a biological material according to the ninth aspect of the present invention, a liquid passage through which the mixture solution can pass, is provided in the packing unit. Therefore, by drawing and discharging the solution, the mixture solution can be readily put into the packing unit or discharged. Moreover, by causing various relative motions between the host contained in the mixture solution which is mixed by the drawing and discharging motion, and the magnetic support which is moved by the magnetic source, the chance of collision or encounter can be increased.

A tenth aspect of the present invention is an apparatus for introducing a biological material provided with a transfer mechanism which enables relative movement between the packing unit and the position of the introduction treatment where the introduction treatment unit can perform the introduction treatment with respect to the packing unit. Here, the position of the introduction treatment is for example a position where the magnetic source is close thereto. The movement by the transfer mechanism, and the movement of the magnetic source or the packing unit for the introduction treatment by the introduction treatment unit are generally different, but may be performed using a common mechanism.

In the tenth aspect of the present invention, the transfer mechanism which enables relative movement of the packing unit between the positions of the introduction treatment where the introduction treatment unit can perform the introduction treatment with respect to the packing unit is provided. Therefore, it is not necessary to provide an apparatus required to perform the introduction treatment, for example the magnetic source, close to the respective packing units. It is sufficient to move the packing unit to the position where the apparatus required to perform the introduction treatment, for example the magnetic source, is used, only when performing the introduction treatment. Therefore, it is sufficient to provide a small number of positions of the introduction treatment for a large number of packing units, thus enabling simplification of the apparatus structure and a reduction in manufacturing cost. Moreover, since it is not necessary to provide the magnetic source close to the respective packing units, the apparatus structure can be integrated and manufactured in a compact size. Furthermore, by preparing the positions of the introduction treatment so as to have a magnetic source which applies various magnetic forces according to purpose, various introduction treatments can be performed for one packing unit, and hence the variety and generality are high. Moreover, various treatments including the introduction treatment can be standardized and automatically performed using the packing unit.

An eleventh aspect of the present invention is an apparatus for introducing a biological material wherein the magnetic source comprises a plurality of electromagnets provided around the packing unit, and the magnetic force control unit electrically modifies the magnitude of the magnetic force of the electromagnets. The magnetic support is moved toward the larger magnetic force until the magnitude of the magnetic force is modified at a certain distance, and then it is moved in the opposite direction. By controlling to repeat this process, the chance of collision or encounter of the magnetic support with the host can be promoted. In this case, if the respective pair of electromagnets of the magnetic source are arranged to face each other around the packing unit with the packing unit therebetween for example, and are controlled so as to switch the magnetic force, the magnetic support can be readily reciprocated in the solution and the magnetic supports can be moved around for a long time extensively.

In the eleventh aspect of the present invention, since the plurality of electromagnets serving as the magnetic source are arranged around the packing unit and the introduction treatment is performed only by controlling the magnitude of the magnetic force, it is not necessary to provide a mechanically movable part, thus simplifying the structure and elongating the life of the apparatus.

A twelfth aspect of the present invention is an apparatus for introducing a biological material having a plurality of permanent magnet blocks or electromagnets serving as the magnetic source which are movably provided around the packing unit, and the magnetic force control unit moves the magnetic sources with respect to the packing unit. The magnetic sources are moved for example, to come closer, away, vertically or in the circumferential direction with respect to the packing unit. At this time, by providing the respective pairs to face each other with the packing units therebetween and making the magnetic source closer and apart, periodic movement such as reciprocation become readily possible so that the magnetic supports can be moved around for a long time extensively.

In the twelfth aspect of the present invention, the plurality of permanent magnet blocks or electromagnets serving as the magnetic source are movably provided around the packing unit, and the magnetic source is made closer and apart, so that various complex movements such as oscillation, accelerated motion, or the like can be produced.

A thirteenth aspect of the present invention is an apparatus for introducing a biological material wherein the magnetic source is an annular magnet having predetermined magnetic poles which are arranged around the packing unit in a circular tubular shape, and the magnetic force control unit has: a magnetic source transfer unit which enables movement of the magnetic source along the radial direction, axial direction, and the circumferential direction of the packing unit or a packing unit transfer unit which enables movement of the packing unit; or a mixture solution transfer unit which moves the mixture solution.

The "mixture solution transfer unit which moves its mixture solution" is to move the mixture solution within the packing unit. If there is a liquid passage, it corresponds to the pressure adjuster which can draw and discharge the mixture solution. The axis of the annular magnet is preferably movable approximately coaxially in parallel, or inclined with respect to the axis of the packing unit. The magnetic poles are preferably distributed approximately evenly in as wide a range as possible along the torus so that the magnetic forces can be applied firm many directions as the "predetermined magnetic poles". Accordingly, the magnetic supports can be distributed to divide the packing unit into upper and lower parts in a layered planar form. Therefore, by moving the layer vertically, the chance of widely encountering with the host in the solution is further increased.

In the thirteenth aspect of the present invention, the annular magnet around the packing unit is used so as to readily apply the magnetic forces to the packing unit from many directions, so that the magnetic supports are developed in higher density in a planar shape than in other areas so as to approximately partition the packing unit inside the packing unit and be moved in a predetermined direction, thus increasing the chance of collision or encounter of the magnetic support with the host. Moreover since the number of magnets is only one, the apparatus structure or the support structure is simplified.

A fourteenth aspect of the present invention is an apparatus for introducing a biological material wherein a plurality of the packing units are arranged along a horizontal line, and the introduction treatment unit has: two linear magnetic sources provided with the packing unit therebetween along the horizontal line, and having magnetic poles provided respectively in positions corresponding to the respective packing units; and a magnetic force control unit which enables relative movement between the magnetic supports and the host by changing the relative position between the packing unit or the mixture solution and the linear magnetic sources, or changing the magnetic force itself due to the linear magnetic sources.

Here, "changing the relative position between the packing unit or the mixture solution and the linear magnetic sources" means for example, to move the linear magnetic sources closer, away, vertically, or horizontally with respect to the packing unit or the mixture solution. Alternatively, it means to move the packing unit closer, away or vertically or horizontally with respect to the linear magnetic sources, to rotate the respective packing units about their axes, or to move the mixture solution with respect to the packing unit. Accordingly the direction of the magnetic fortes of the linear magnetic sources can be controlled to apply from various directions, so that the number of collisions or the rate of collision or the chance of encounter can be increased.

In the fourteenth aspect of the present invention, a plurality of packing units are arranged in parallel in a horizontal line, and the magnetic sources in the horizontal line are arranged with the packing units therebetween, along the lines of the packing units. Therefore, the apparatus structure can be simplified and the introduction treatment can be integrally performed, so that the introduction treatment can be further effectively performed.

A fifteenth aspect of the present invention is an apparatus for introducing a biological material wherein the linear magnetic source has two linear support bodies provided on opposite sides with the arrayed packing units therebetween, along the horizontal line, and a plurality of permanent magnets or electromagnets arranged at intervals and positions corresponding to the respective packing units, in the linear support bodies.

The permanent magnet or the electromagnet may be formed by bending into semiannular shapes around half portions of the packing unit respectively so as to apply the magnetic threes from many directions.

In the fifteenth aspect of the present invention, the linear magnetic sources are arranged at intervals and positions corresponding, to the packing units arranged in the linear support bodies. Therefore, the permanent magnets or the electromagnets are arranged for each of the packing units, thus simplifying the structure and facilitating the treatment.

A sixteenth aspect of the present invention is an apparatus for introducing a biological material wherein each of the packing units has a liquid passage through which a mixture solution can pass, and a pressure adjuster which draws and discharges the solution by adjusting the pressure in the liquid passage.

In the sixteenth aspect of the present invention, each packing unit has a liquid passage through which the mixture solution can pass. Therefore, the drawing and discharging of the solution enables relative movement between the host and the magnetic support, increasing the number of collisions or the rate of collisions, or increasing the chance of encounter.

A seventeenth aspect of the present invention is an apparatus for introducing a biological material wherein the introduction treatment unit has a magnetic separation unit whereby hosts having the magnetic support introduced thereinto or adhered thereto, are attached to the inner wall of the packing unit and separated from the mixture solution in the packing unit, by controlling the magnetic force applied to the inside of the packing unit.

In order to separate the unused magnetic supports which have not entered into or been adhered to the host, from in the mixture separated by the magnetic force of the magnetic separation unit, it is preferably that a filter having a pore size between the host size and the magnetic support size is provided to partition a predetermined part in the liquid passage, or that a holder having the filter is detachably attached to the tip end of the liquid passage. By doing this, after introduction treatment, the solution suspended with only the mixture separated by the attachment to the inner wall of the packing unit by the magnetic force is drawn and discharged with respect to the packing unit through the filter, so that only the host having the magnetic support entered thereinto or adhered thereto is extracted in the filter, and the unused magnetic supports are removed. Alternatively, the situation may be such that, after introduction treatment, before the separation by the magnetic forte, the mixture solution is drawn and discharged with respect to the packing unit through the filter, so that the unused magnetic supports are removed, and then the separation is performed by the magnetic force so as to extract the host having the magnetic support entered thereinto or adhered thereto.

The liquid passage may be a tip detachably provided on the nozzle of the pressure adjuster. The filter may be provided on the tip. Moreover, in order to remove various other impurities except for the target host, one or more filters having different pore sizes may be provided in the liquid passage or the holder. Furthermore, a plurality of holders provided with the filters may be detachable in multi-stages with respect to the liquid passage. Accordingly, only the host having the magnetic support entered thereinto or adhered thereto, that is the host having the target biological material introduced can be separated, so that unnecessary substances such as the unused magnetic supports, impurities, and the like are removed, so that reliable introduction of the biological material can be performed.

In the seventeenth aspect of the present invention, regarding the magnetic separation unit by which the hosts having the magnetic support introduced thereinto or adhered thereto are attached to the inner wall of the packing unit to be separated by the magnetic force, the magnetic source which is used for increasing the chance of collision or encounter of the magnetic support with the host may be used, so that the structure can be simplified and the separation can be efficiently and quickly performed.

An eighteenth aspect of the present invention is an apparatus for introducing a biological material wherein then magnetic separation unit has a separation instruction unit which instructs the magnetic force transfer control unit to apply only a unidirectional magnetic fame towards the wall of the packing unit.

Accordingly, the magnetic support collides with the inner wall of the packing unit along the above direction, and is attached thereto.

In the eighteenth aspect of the present invention, it is sufficient if the magnetic separation unit merely instructs the magnetic source to apply only the unidirectional magnetic force towards the wall of the packing unit. Hence the structure can be simplified and the manufacturing cost can be reduced.

A nineteenth aspect of the present invention is a method of introducing a biological material comprising: a mixing step wherein a large number of magnetic supports carrying a biological material introduced into a host such as a cell, and a large number of the hosts are mixed in a solution to make a mixture solution, which is then put into one or more packing units; and an introduction treatment step wherein the magnetic supports are moved relatively with respect to the host by controlling a magnetic force applied to the packing unit so as to introduce the biological material into the host.

In the present invention, by moving the magnetic supports around with respect to the host in the solution in the packing unit by the magnetic force, the chance of collision or encounter with the host suspended or contained in the solution can be increased. Accordingly, the introduction of the biological material into the host is promoted. At this time, if the magnetic force is applied from at least two directions with the packing therebetween, the movement of the magnetic supports is not finished by being attached to the packing unit in the solution only by a unidirectional motion by the magnetic force applied, but can be continued in the solution for a long time by releasing the attachment state, or by initially avoiding the attachment state.

According to the nineteenth aspect of the present invention, similar effects to those described in the first aspect of the present invention are demonstrated.

A twentieth aspect of the present invention is a method of introducing a biological material wherein in the introduction treatment step, the magnetic supports and the host are moved relatively to each other by changing the relative position or the velocity between the packing unit or the mixture solution and the magnetic field, or the magnetic force itself.

Here, by applying the magnetic force from at least two directions with the packing unit therebetween, from the outside of the packing unit into the packing unit, the magnetic supports are moved around in the solution avoiding a situation such as where the magnetic supports are attached onto the packing unit or precipitated at the bottom of the packing unit by a unidirectional magnetic force, so that the chance of collision or encounter with the host can be increased and the introduction of the biological material into the host can be promoted.

According to the twentieth aspect of the present invention, similar effects to those described in the second aspect of the present invention are demonstrated.

A twenty-first aspect of the present invention is a method of introducing a biological material wherein in the introduction treatment step, the magnetic supports and the host are moved relatively to each other in a state where a large number of the magnetic supports in the solution contained in the packing unit are developed solution by the magnetic force.

According to the twenty-first aspect of the present invention, similar effects to those described in the third aspect of the present invention demonstrated.

A twenty-second aspect to the present invention is a method of introducing a biological material wherein, the introduction treatment step uses a magnetic support being a particle having one major axis, and having a size allowing entry into a host along the major axis direction, and moves the magnetic support to enter the host so as to introduce the biological material. Here, the magnetic support is magnetized or formed to be easily magnetizable, in the major axis direction, so as to enable the magnetic support to be moved in the major axis direction, thus facilitating the entry using the magnetic force.

According to the twenty-second aspect of the present invention, similar effects to those described in the fourth aspect of the present invention are demonstrated.

A twenty-third aspect of the present invention is a method of introducing a biological material comprising a separation step after the introduction treatment step wherein the host having the magnetic support entered thereinto or adhered thereto is attached to the inner wall of the packing unit and separated, by controlling the magnetic force inside of the packing unit.

After the separation step, a removal step wherein unused magnetic supports which did not enter into or were not adhered to the host and the like are removed from among the substances attached to the inner all of the packing unit. The removal step is performed for example, by using a filter provided so as to partition the liquid passage provided in the packing unit, or a holder having a filter detachably attached to the liquid passage, and drawing and discharging a solution with respect to the packing unit and the like through the filter. Moreover, a removal step may be provided for removing one or more other impurities except for the magnetic support using one or more types of filter. Accordingly, an even more reliable introduction treatment can be performed.

Furthermore, according to the twenty-third aspect of the present invention, similar effects to those described in the seventeenth aspect of the present invention are demonstrated.

A twenty-fourth aspect of the present invention is a method of introducing a biological material wherein the mixing step mixes the magnetic support and the biological material to be introduced into the host in solution, so that the biological material is carried in the magnetic support.

According to the twenty-fourth aspect of the present invention, by mixing the magnetic support and the biological material to be introduced into the host in solution, the biological material can be readily carried, making it suitable for automating the treatment.

A twenty-fourth aspect of the present invention is a method of introducing a biological material comprising a culturing step wherein after the separation step, in a state where the separated hosts having the magnetic support adhered thereto or entered thereinto are pooled in the packing unit, the hosts are relatively moved to inside a container containing a medium and the hosts are pooled in the container and cultured.

According to the twenty-fifth aspect of the present invention, in the state where the host having the magnetic support entered thereinto or adhered thereto are separated by using the magnetic force and attached to the inner wall of the packing unit, the host can be relatively moved to inside into the container containing the medium and put into the medium, enabling the culturing treatment to be performed automatically. Therefore the treatment can be standardized and automatically performed.

A twenty-sixth aspect of the present invention is a method of introducing a biological material wherein in the culturing step, the hosts having the magnetic support entered thereinto or adhered thereto are separated and removed from the cultured hosts by applying a magnetic force, so as to exclusively obtain purely cultured hosts.

According to the twenty-sixth aspect of the present invention, the host having the magnetic support entered thereinto or adhered thereto, and which has initially been placed into the medium in the culturing step, can be cultured while initially being separated from the cultured host by applying the magnetic force. Therefore, the host having the magnetic support entered thereinto or adhered thereto can be readily removed. Accordingly, a purely cultured host can be exclusively obtained easily and reliably. Therefore, the negative affect to the organism due to the presence of the magnetic support in the cell can be removed.

A twenty-seventh aspect of the present invention is a method of introducing a biological material comprising: an introduction step for making magnetic supports carrying the biological material to be introduced into the host collide or encounter with the host using a magnetic force so as to introduce the biological material into the host; a separation step for separating the host having the magnetic support entered thereinto or adhered thereto; a culturing step for culturing the host using the separated host; and an extraction step for extracting a purely cultured host by separating the host which initially has the magnetic support entered thereinto or adhered thereto, from inside the cultured host. Here, the separation step preferably includes an impurities removal step for removing unused magnetic supports which were not adhered to or did not enter into the host, and foreign matter or impurities using a filter.

According to the twenty-seventh aspect of the present invention, the treatment from the introduction of the biological material into the host, to the culture of the host having the biological material introduced thereinto can be automatically performed and standardized.

A twenty-eighth aspect of the present invention is a magnetic support for introducing a biological material, which is a magnetic support in a particle shape having one major axis, and capable of carrying biological material to be introduced into a host such as a cell, and having a size allowing entry into the host along the major axis direction. Here, the magnetic support is preferably magnetized or formed so as to be easily magnetized, along the major axis direction, and is formed so as to be readily moved along the major axis direction under control. Moreover, the magnetic support preferably has an axial symmetry in relation to the major axis.

According to the twenty-eighth aspect of the present invention, similar effects to those described in the fourth aspect of the present invention are demonstrated.

A twenty-ninth aspect to the present invention is a magnetic support for introducing a biological material wherein the magnetic support has a carrier for carrying the biological material. Here, the carrier is as described in the sixth aspect to the present invention.

According to the twenty-ninth aspect of the present invention, similar effects to those described in the sixth aspect of the present invention are demonstrated.

A thirtieth aspect of the present invention is a magnetic support for introducing a biological material wherein in the magnetic support, both ends or one end along a major axis are formed in a tapered shape. The degree of tapering is as described in the seventh aspect of the present invention.

Furthermore, according to the thirtieth aspect of the present invention, similar effects to those described in the seventh aspect of the present invention are demonstrated.

The thirty-first aspect of the present invention is an apparatus for introducing a biological material comprising; one or more packing units containing a mixture solution having a large number of magnetic supports carrying a biological material to be introduced into a host such as a cell, and a large number of the hosts in a solution; an introduction treatment unit which moves the magnetic supports relatively with tweet to the hosts in the solution by controlling a magnetic force applied to inside the packing unit so as to introduce the biological material into the host; and a perforation treatment unit which perforates the host.

Here, "perforate the host" means to make holes in a boundary region in contact with the outside of the host so as to facilitate entry of the magnetic support on the outside into the host, or facilitate introduction of the biological material into the host. The perforation treatment is normally performed on the host in the packing unit, however it is not limited to this. If the host is a cell, the boundary is a cell membrane or a cell wall. In order to make holes in the boundary of the host, for example a perforation force is applied to the host by electrical discharge or ultrasound cavitation "Perforation force" means a certain force for making holes on the boundary of the host. In the case of electrical discharge, if the host is a cell, for example, a high voltage of about several thousands of volts/cm is applied at several dozens of microsecond pulses. Moreover, in the case where the magnitude of the voltage is modified, the pulse width may be modified according thereto. If the other conditions are the same, then in the case of low voltage, the pulse width is elongated more than for the case of a high voltage. In the case of high voltage, the pulse width is shortened more than for the case of a low voltage. Accordingly, small holes are made on the boundary of the host, for example the cell membrane for a short time, facilitating making the magnetic support enter into or be introduced to the biological material. According to the present invention, even if the magnetic supports are not collided with the host the entry efficiency of the magnetic support or the introduction efficiency of the biological material to the host may be increased by increasing the chance of encounters of the magnetic support and the host. Therefore, control is facilitated. According to the present invention, the objective of the electroporation for perforating the cell membrane to introduce only the gene on the outside, is expanded to general hosts, and the boundary of the host on the outside is perforated so that the magnetic support can enter the host.

A thirty-second aspect of the present invention is an apparatus for introducing a biological material wherein the introduction treatment unit comprises: a magnetic source which can apply a magnetic force to the inside of the packing unit; and a magnetic force control unit which controls relative movement between the magnetic supports and the host by changing the relative position or the velocity between the packing unit or mixture solution and the magnetic field, or the magnetic force itself due to the magnetic source.

According to the thirty-second aspect of the present invention, similar effects to those described in the second aspect of the present invention are demonstrated.

A thirty-third aspect of the present invention is an apparatus for introducing a biological material wherein the perforation treatment unit has: a perforation force source which can apply a perforation force by an electric field, or ultrasound, or the like; and a perforation force source control unit which controls the perforation force source.

The perforation force source is preferably provided within the packing unit. Accordingly, the perforation three can be reliably and efficiently applied to the host in the packing unit.

If the packing unit has a liquid passage through which the mixture solution can pass and the magnetic force control unit has a pressure adjuster which draws and discharges the solution by adjusting the pressure within the liquid passage, the perforation treatment unit is provided with a perforation force source so as to perform the perforation treatment on the host passing through the liquid passage.

Accordingly, since the treatment by the perforation treatment unit is performed in the liquid passage, the perforation treatment can be applied efficiently to the host passing through the liquid passage.

Moreover, if the packing unit has a storage unit which stores a mixture solution, the perforation treatment unit may be provided with a perforation force source so as to perform perforation treatment on the host in the mixture solution stored in the storage unit. Accordingly, since in this case the perforation treatment is performed at the position where the introduction treatment is performed, the entrance of the magnetic support into the perforated host is further readily controlled.

The perforation force source is not necessarily provided on the packing unit, but may be provided in an external container for containing the solution to be supplied to the packing unit. Accordingly, the perforated host can be drawn into the packing unit.

The control of the perforation force tree includes the control of the type, position, the size, the direction, or the time of the perforation force.

If electrical discharge is used as the perforation force, the perforation force source is a pair of facing electrodes. If ultrasound is used as the perforation force, the perforation force source is an ultrasonic oscillator. The selection of the voltage to be applied to the electrode, and the selection of positive electrodes and negative electrodes may be changed according to the size, the position, or the operating direction of the biological material to be introduced, the host, or the magnetic support, or according to the position or the control of the magnetic source, or according to the time. Accordingly, the entrance of the magnetic support or the introduction of the biological material can be further efficiently performed. Moreover, the arrangement may be such that both of electrical discharge and ultrasound as the perforation force source are applied to the host in the packing unit. For that purpose, a plurality of types of perforation force sources are provided.

A thirty-fourth aspect of the present invention is an apparatus for introducing a biological material wherein the perforation force source control unit controls the perforation force source based on the properties, the amount, or the density of the host, the biological material, or the magnetic support.

Accordingly, by applying the optimum perforation force to the host or the like being used, the biological material can be reliably and efficiently introduced.

Here, "properties" includes the physical properties such as the size, the hardness, and the shape, and the chemical properties such as molecular structure, repairability, and the like.

A thirty-fifth aspect of the present invention is an apparatus for introducing a biological material wherein the perforation force source unit or the magnetic force control unit control the introduction treatment and the perforation treatment so as to be executed in spatial or time association with each other.

The reason for this is that the perforation provided in the host by the perforation treatment unit may be repaired in a short time, thus requiring consideration of the respective positions and the limes to perform the perforation treatment and the introduction treatment.

Moreover, if the magnetic three is controlled to match the direction of the perforation treatment of the host so as to move the magnetic support in the direction of the host, the magnetic support readily enter the host.

A thirty-sixth aspect of the present invention is an apparatus for introducing a biological material wherein the packing unit has a liquid passage through which the mixture solution can pass, and has a pressure adjuster which draws and discharges the solution by adjusting the pressure in the liquid passage, as the magnetic force control unit. According to the thirty-sixth aspect of the present invention, similar effects to those described in the ninth aspect of the present invention are demonstrated.

A thirty-seventh aspect of the present invention is a method of introducing a biological material comprising: a mixing step wherein a large number of magnetic supports carrying a biological material to be introduced into a host such as a cell, and a large number of the hosts are mixed in a solution to make a mixture solution, which is then put into one or more packing units; a perforation treatment step which perforates the host such as a cell; and an introduction treatment step wherein the magnetic supports are moved relatively with respect to the host by controlling a magnetic force applied to the packing unit, so as to introduce the biological material into the host.

Here, the perforation treatment step is not necessarily performed after the mixing step, and may be performed in an external container before the mixing step, so as to mix the perforated host.

Moreover, if the perforation treatment step comes after the mixing step, the perforation treatment is performed within the packing unit.

According to the thirty-seventh aspect of present invention, even if the magnetic supports are not collided with the host, the entry efficiency of the magnetic support or the introduction efficiency of the biological material to the host, may be increased by increasing the chance of encounter of the magnetic support and the host. Therefore, the control is facilitated.

A thirty-eighth aspect of the present invention is a method of introducing a biological material wherein the perforation treatment step is performed by applying a perforation force such as an electric field, ultrasound, or the like.

According to the thirty-eighth aspect of the present invention, similar effects to those described in the thirty-third aspect of the present invention are demonstrated.

A thirty-ninth aspect of the present invention is a method of introducing a biological material wherein the perforation treatment step applies the perforation force based on the properties, the amount, or the density of the host, the biological material, or the magnetic support.

According to the thirty-ninth aspect of the present invention, similar effects to those described in the thirty-fourth aspect of the present invention are demonstrated.

A fortieth aspect of the present invention is a method of introducing a biological material wherein the perforation treatment step and the introduction treatment step are executed in spatial or time association with each other.

According to the fortieth aspect of the present invention, similar effects to those described in the thirty-fifth aspect of the present invention are demonstrated.

The forty-first aspect of the present invention is an apparatus for introducing a biological material which further comprises: a transfer device which separates and transfers a solution containing a host which has been treated by the introduction treatment unit, and has the magnetic support adhered thereto or entered thereinto, or a host having the magnetic support adhered thereto or entered thereinto; a container containing a medium; and a separation unit for separating the magnetic support contained in the container and the host having the magnetic support adhered thereto or entered thereinto.

Here, the separation unit may be for example, a magnetic force unit comprising a permanent magnet or an electromagnet provided at the bottom or the lateral side of a container formed of a resin or the like which does not shield the magnetic field; or may be a dispenser which has a liquid passage, a pressure adjustment device which adjust the pressure within the liquid passage, and a magnetic force device which can apply the magnetic force from the outside of the liquid passage into the liquid passage, with a transfer function. In the case of a container comprising a plurality of holes, the permanent magnet or the electromagnet is preferably provided for each of the respective holes.

According to the forty-first aspect of the present invention, by applying the magnetic force to the container containing the medium, the host having the magnetic support altered thereto or entered thereinto can be separated, so that the purely cultured host with a simple structure can be easily obtained. Hence safe and reliable introduction treatment can be performed.

BRIEF DESCRIPTION OF THE DRAWINGS

FIG. 3 is a plan view and an elevational view of a biological material introduction system according to a second embodiment of the present invention.

FIG. 15 shows a separation unit of an apparatus for introducing a biological material according to a seventh embodiment of the present invention.

BEST MODE FOR CARRYING OUT THE INVENTION

An apparatus for introducing a biological material and a method of introducing a biological material according to embodiments of the present invention are described based on the drawings. The description of the present embodiments should not be considered as limiting the present invention unless particularly specified.

Figure 1:
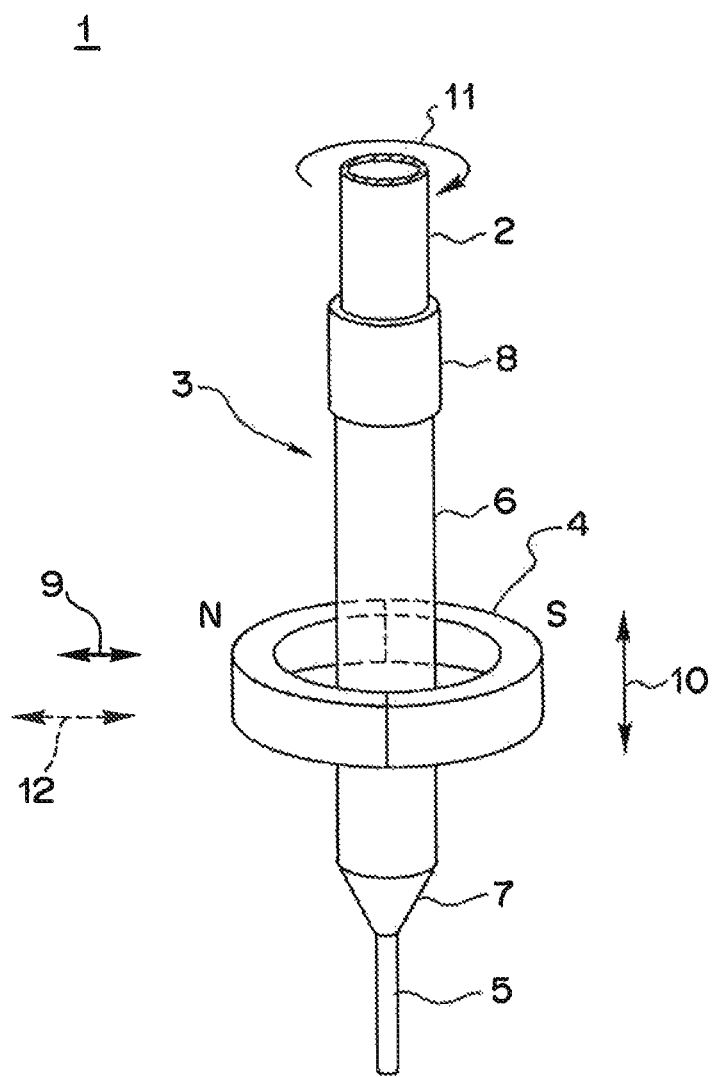
FIG. 1 show a main part of an apparatus for introducing a biological material according to a first embodiment of the present invention.

FIG. 1 shows a main part of an apparatus 1 for introducing a biological material according to a first embodiment.

The apparatus 1 for introducing a biological material has an approximately circular tubular tip 3 which is detachably attached to a nozzle 2, an annular permanent magnet 4, and a magnetic source transfer unit (not shown). The tip 3 corresponds to one packing unit in which a mixture solution containing a large number of magnetic supports can a biological material to be introduced into a host such as cells upon use, together with a large number of the hosts are pooled. The annular permanent magnet 4 corresponds to a magnetic source which is movably provided for controlling a predetermined magnetic force so that the magnetic supports in the solution in the tip 3 are moved relatively between the magnetic supports and the hosts, making the magnetic supports collide with or encounter the hosts. Moreover, the magnetic source transfer unit is for moving the annular permanent magnet 4 with respect to the tip 3.

The tip 3 has a small diameter liquid passage 5 which is for drawing and discharging a liquid with respect to a container (not shown) provided outside, a large diameter storage unit 6 which stores the mixture solution containing the magnetic supports, and a hollow middle diameter unit 7 in an approximately truncated conic shape which is provided between the liquid passage 5 and the storage unit 6. The axis of the annular permanent magnet 4 is desirably provided in an approximate coaxial manner, inclined, or in parallel with respect to the axis of the storage unit 6, so that the annular permanent magnet 4 is movable in the axial, radial, and circumferential directions, and optional combination thereof around the storage unit 6.

Moreover, an attachment unit 8 for attaching the nozzle 2 on the top of the storage unit 6 is provided. The nozzle 2 is communicated with a piston via a duct (not shown) and corresponds to a pressure adjuster.

The annular permanent magnet 4 is a combination of two semiannular permanent magnets. One semiannular permanent magnet has a north pole in an area including the center, and south poles on the opposite ends. The other semiannular permanent magnet has a south pole in an area including the center, and north poles on the opposite ends. These opposite ends are connected and formed into an annular shape. Lines of magnetic force are distributed such that the density of two portions including the centers which face each other with the storage unit 6 of the tip 3 being the packing unit therebetween, is even and the highest, and the density gets lower as it goes away from the area along the torus.

In FIG. 1, the annular permanent magnet 4 can be oscillated in the directions shown by the arrows 9 and 10 in a solid straight line, by the magnetic force transfer unit. Moreover, the nozzle 2 and the tip 3 attached thereto can be rotated by a nozzle rotation unit (not shown) in a direction shown by the arrow 11 in a solid curved line.

The arrow 12 in a broken line represents a case where an attempt is made to separate the magnetic supports by making them attach to the wall of the tip 3, moving the annular permanent magnet 4 along the direction linking the magnetic poles, so that only one magnetic pole comes sufficiently close to the storage unit 6 of the tip 3. These magnetic source transfer unit, nozzle rotation unit, and pressure adjuster constitute the magnetic force control unit, which constitutes the introduction treatment unit together with the annular permanent magnet 4 being the magnetic source.

Figure 2:
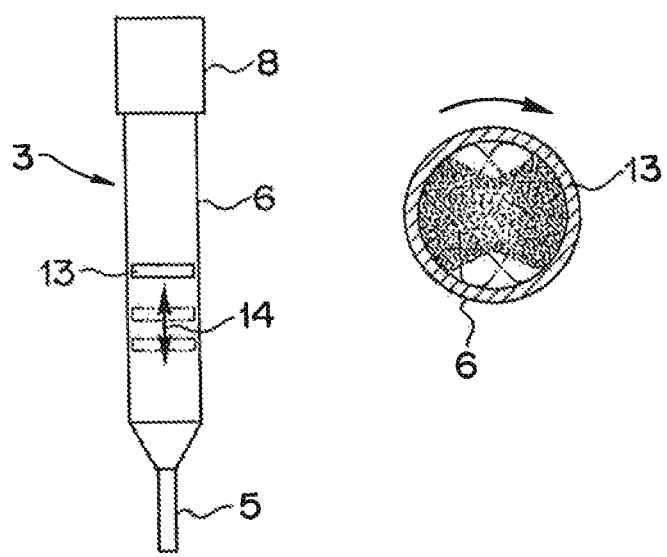
FIG. 2 is an explanatory diagram of the operation of the apparatus for introducing a biological material according to the first embodiment of the present invention.

FIG. 2 explains the operation of the apparatus 1 for introducing a biological material shown in FIG. 1.

A mixture solution containing the magnetic supports carrying the biological material to be introduced into cells being a host drawn from an external container through the liquid passage 5 of the tip 3, and the cells being the host, are placed in the storage unit 6. At this time, the magnetic force due to the annular permanent magnet 4 affects the magnetic supports contained in the mixture solution.

Moreover, due to the annular permanent magnet 4, magnetic forces of approximately identical degree influence the magnetic supports mainly from two facing directions with the tip 3 therebetween. Therefore the balance of the respective magnetic supports is maintained where the combined magnetic forces almost cancel each other, keeping the magnetic supports from being attracted unilaterally to one direction, and to not be attached to the wall of the tip 3. The magnetic supports are also kept from falling down due to the gravity, by the magnetic force, and the magnetic supports are developed in a high density in a layered planar shape in the solution. As shown in FIG. 2(a), the magnetic supports in the mixture solution form a horizontal planar magnetic support layer 13 in an approximate letter 8 shape as shown in FIG. 2 (*b*) at the height where the annular permanent magnet 4 is present.

Regarding the magnetic support layer 13 in such a developed state, the annular permanent magnet 4 is oscillated and repeatedly moved along the vertical arrow 10 by the magnetic source transfer unit (not shown) and the nozzle 2 is rotated by the nozzle rotation unit. In consequence, the magnetic support layer 13 is oscillated in the direction of the anew 14 as shown in FIG. 2(*a*), and the layer 13 is rotated in the tip 3 as shown by the arrow in FIG. 2 (*b*).

Accordingly, the magnetic support layer 13 is extended to partition the tip 3 into upper and lower parts horizontally as if it is a filter or a paper provided approximately in the middle of the tip 3. Therefore the vertical oscillation of the magnetic support layer 13 using the magnetic source transfer unit can promote a closer approach of the magnetic supports to the hosts diffused in the solution passing through the magnetic support layer 13, and can increase the number of collisions or the rate of collision, or increase the chance of encounter.

As a result, it becomes highly possible that the hosts in the solution collide with or encounter the magnetic supports constituting the magnetic support layer 13, making the magnetic supports come in contact with the hosts, making the magnetic supports adhere to the hosts, or making the magnetic support enter the hosts.

Next is a description of a biological material introduction system 15 according to a second embodiment based on FIG. 3 to FIG. 9. The same reference symbols are used for components the same as those described in the first embodiment, and the description thereof is omitted.

As shown in a plan view of FIG. 3 (*a*), the biological material introduction system 15 has: a stage 16 on which the biological material introduction treatment is performed; a set of eight nozzles unit 17 having the abovementioned nozzles 2 provided for the stage 16, and arranged at intervals along a horizontal line with the respective axes thereof vertical and in parallel, with the tips 3 detachably attached to the nozzles 2 respectively; reagent baths 18 provided with various mediums according to the host type; tip racks 19 having unused tips 3 to be attached to the set of eight nozzles 2 arranged in a matrix form of eight columns plate 21 having solution packing units 20 arranged in a matrix form of 8 columns×12 rows for containing a solution for performing the biological material introduction treatment, that is, a mixture solution containing a large number of magnetic supports carrying a target biological material to be introduced into a host such as cells, and a large number of hosts, mixed in solution; a container 23 comprising solution packing units 22 of 8 columns×2 rows containing DNA solution; and a container 25 comprising solution packing units 24 of 8 columns×2 rows containing a solution suspended with cells as the host. One row of the solution packing units in the container 25 is a container 26 for PCR.

Furthermore, the stage 16 has; a magnetic force treatment unit 27 corresponding to the introduction treatment unit, by which a magnetic force can be applied to the tips 3 attached to the set of eight nozzles 2 all at once; a container 29 comprising solution packing units 28 of 8 columns×2 rows for containing the introduced result; and a waste vent 30 for disposing the used tips 3. Reference symbols 31, 32, and 33 denote heated/cooled areas where a temperature control unit for heating or cooling the containers in the respective areas is provided, enabling control of the temperature.

The set of eight nozzles unit 17 has the set of eight nozzles 2 and the set of eight tips 3 attached thereto. A nozzle head 77 provided with various mechanical sections is provided to the nozzle unit 17. The nozzle head 77 is provided with a Z-axis driving motor 81 which vertically moves the nozzle unit 17.

Moreover, the biological material introduction system 15 has a Y-axis conveyer 82 which can move the nozzle head 77 in the Y-axis direction, and an X-axis conveyer 83 which can move the nozzle head 77 in the X-axis direction. Therefore, the nozzle head 77 is movable horizontally and vertically within the area on the stage 16. Reference symbol 84 denotes a motor for driving the X-axis conveyer 83. As shown in the front view of FIG. 3 (*b*), the motor 84 moves the nozzle head 77 in the X-axis direction by driving to rotate the belt 85. Here, the Y-axis conveyer 82, the X-axis conveyer 83, and the Z-axis driving motor correspond to the transfer unit.

Reference symbol 86 denotes a P-axis motor which drives the piston in the pressure adjuster communicated with the nozzle 2 to adjust the pressure in the nozzle 2 and the tip 3. The P-axis motor 86 drives to rotate a ball screw 88 via a coupling 87. A nut 89 into which the ball screw 88 is threaded, is fixed to props 89*b* and 89*c* for guiding via a plate 89*a*. Therefore, the ball screw 88 is vertically moved by the rotation, which moves a set of eight pistons (not shown) provided on a member 90 which is provided at the bottom of the ball screw 88, vertically all at once. Reference symbol 80 denotes a part provided with a rotating mechanical section for rotating the nozzle 2 around it axis.

Figure 4:
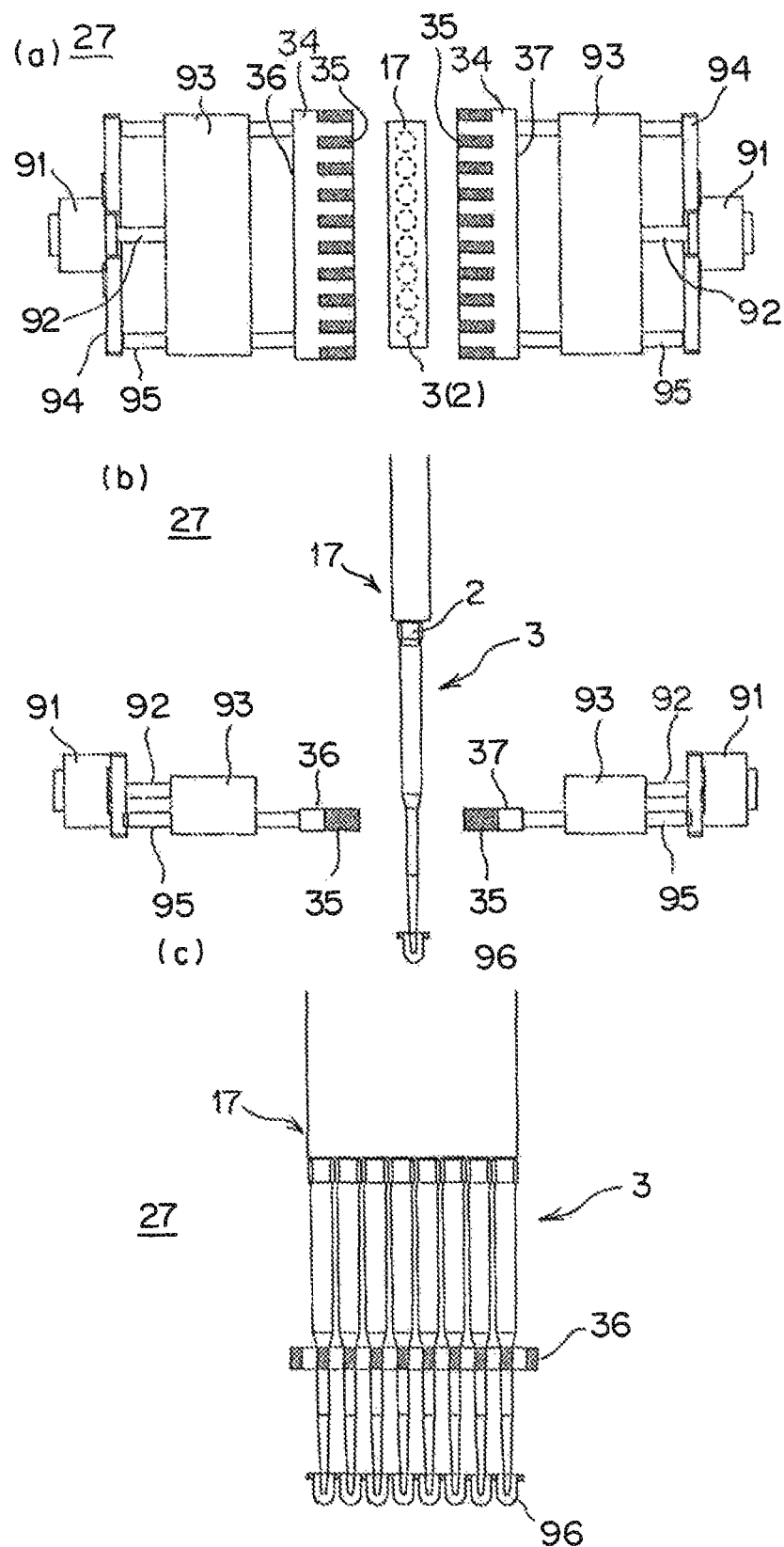
FIG. 4 shows the apparatus for introducing a biological material according to the second embodiment of the present invention.

FIG. 4 shows the magnetic force treatment unit 27 in a state where the point of the tip 3 attached to the respective nozzles 2 of the nozzle unit 17 is inserted into the respective holes 96.

In order to apply the magnetic force to the inside of the tip 3, the nozzle unit 17 is moved to the magnetic force treatment unit 27 by the transfer mechanisms 82 and 83 on the stage 16, and the tip 3 is inserted into the magnetic force treatment unit 27.

As shown in FIG. 4, the set of eight nozzles 2, and therefore the tips 3, are arranged along the horizontal line. Moreover, the magnetic force treatment unit 27 has two linear magnetic sources 36 and 37 which have rod-shaped supporting sections 34 provided on the opposite sides with the tip 3 therebetween, in parallel along the horizontal line, and eight permanent magnet blocks 35 set in positions corresponding to the respective tips 3.

Here, the magnetic poles of the facing magnet blocks 35 of the respective linear magnetic sources 36 and 37 may be the same or different for the south poles and the north poles. Moreover, the magnetic poles of the respective linear magnetic sources 36 and 37 may be arranged to be alternately different in some cases, while the same magnetic poles may be arranged in other cases.

The respective linear magnetic sources 36 and 37 are provided so as to be able to come closer or go away with respect to the nozzle unit 17 by a close/away direction transfer mechanism, and so as to be movable along the array direction of the nozzles 2 of the nozzle unit 17 by an array direction transfer mechanism. The close/away direction transfer mechanism has: motors 91; ball screws 92 driven to rotate by the motors 91; holddown members 93 which are provided so as to be threaded by the ball screws 92 and fixed to the respective floor boards (not shown) of the array direction transfer mechanism which is movably provided with respect to the stage 16 in the horizontal plane; two props 95 which are inserted through the holddown members 93 and connected with the supporting sections 34; and movable members 94 which support the motors 91, the ball screws, and the props 95. The supporting sections 34 can be moved back and forth with respect to the nozzle unit 17 by driving the motors 91. The array direction transfer mechanism is a mechanism to move the linear magnetic sources 36 and 37 separately by a predetermined distance (about the distance between adjacent nozzles 2) in the horizontal plane along the array direction of the nozzles 2 of the nozzle unit 17. The array direction transfer mechanism is provided with the two floor boards which are separately provided so as to be movable along the rail (not shown) along the array direction, provided on the stage 16, instead of the linear magnetic sources 36 and 37 of the close/away direction transfer mechanism, and is respectively provided with hold-down members fixed to the stage 16, instead of the hold-down members 93.

In this manner, with respect to the tip 3, the lines of magnetic force can be moved by moving the tip 3 itself in the Z-axis direction, the lines of magnetic force can be moved by moving the supporting sections 34 freely back and forth with respect to the tip 3, and the lines of magnetic force can be moved by moving the supporting sections 34 horizontally along the array direction of the nozzles 2. Here, the transfer mechanism corresponds to the magnetic some transfer unit.

Figure 5:
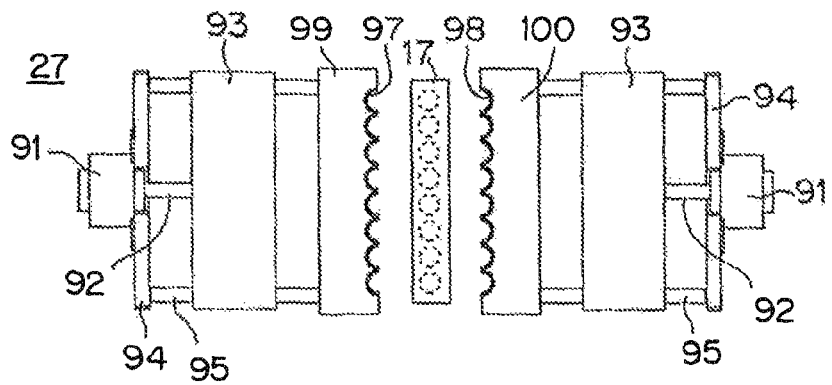
FIG. 5 is a plan view showing another example of an apparatus for introducing a biological material according to the second embodiment of the present invention.

An example shown in FIG. 5 illustrates linear magnetic sources 99 and 100 on which semiannular permanent magnets 97 and 98 are arranged at intervals corresponding to the respective tips 3. The semiannular permanent magnets 97 and 98 respectively correspond to the two semiannular permanent magnets of the annular permanent magnet 4 described in FIG. 1.

Figure 6:
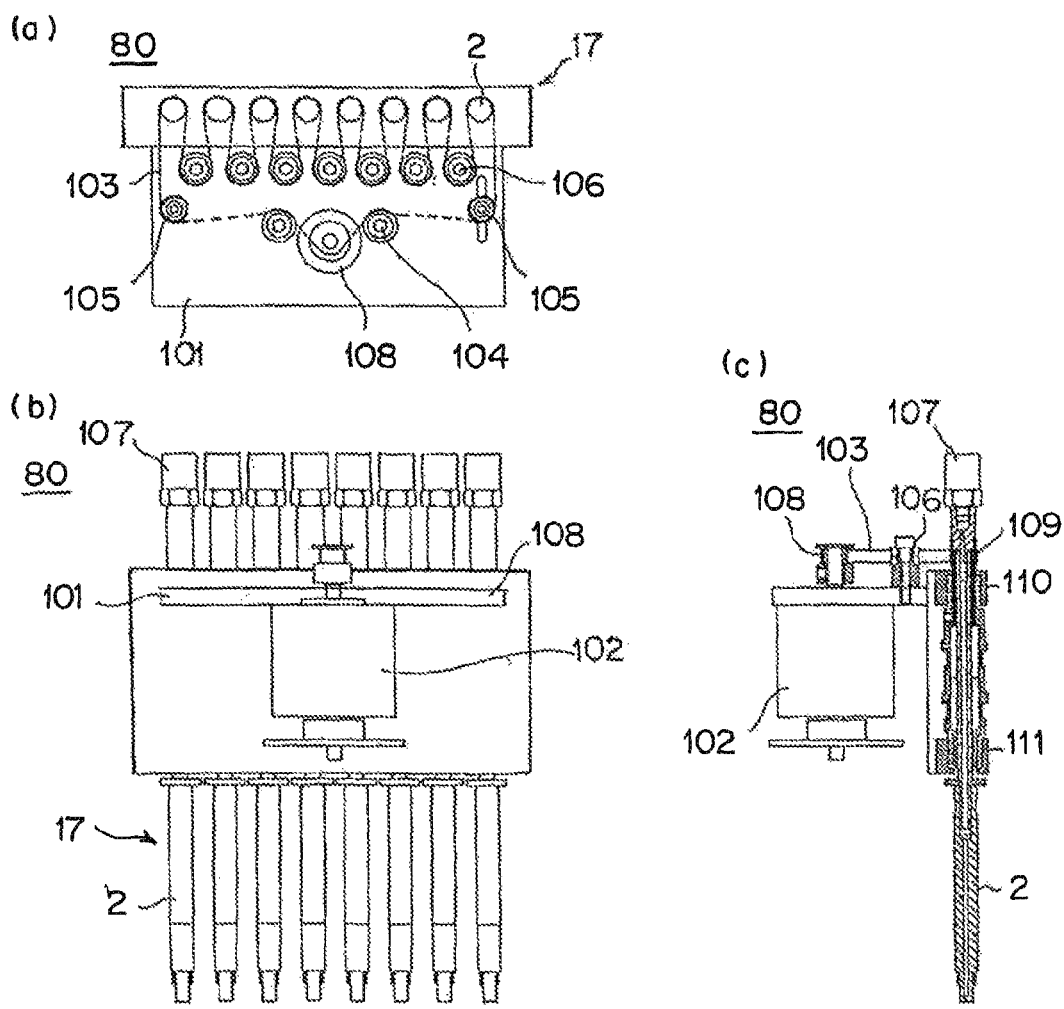
FIG. 6 shows a nozzle head according to the second embodiment of the present invention.

FIG. 6 shows the rotating mechanical section 80 provided in the nozzle unit 17. The rotating mechanical section 80 has: a support plate 101; a motor 102 which is provided on the support plate 101, for rotating the respective nozzles 2 about their axes; and a timing belt 103 which is provided above the support plate 101 and spanned around a driving pulley 108 of the motor 102, nozzle pulleys 109 provided for the respective nozzles 2, and pulleys 104, 105, and 106, to rotation chive the nozzles 2. Reference symbol 107 denotes a rotary joint for rotatably connecting along the axial direction, and the piston is connected at the top. Reference symbols 110 and 111 denote bearings.

Figure 7:
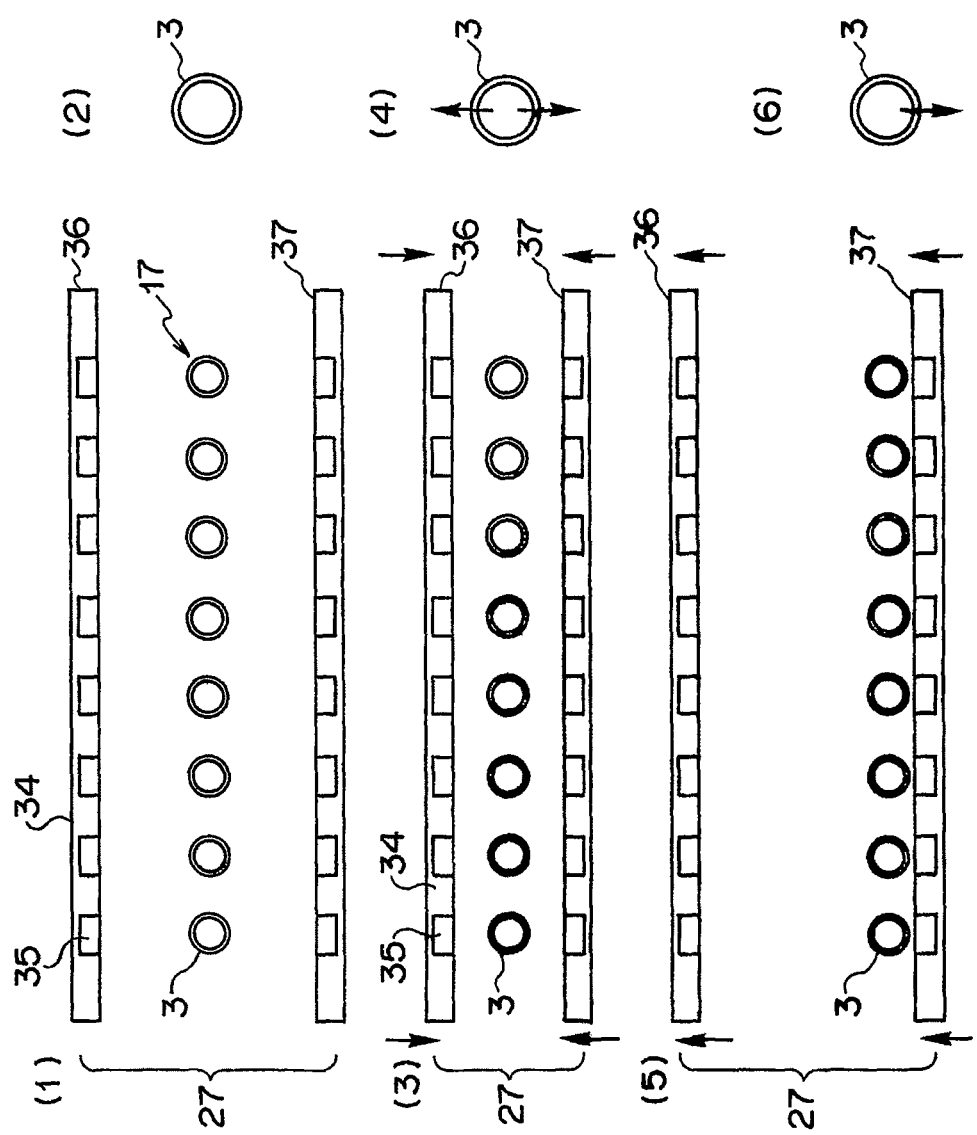
FIG. 7 is an explanatory diagram of the operation of the apparatus for introducing a biological material according to the second embodiment of the present invention.
Figure 8:
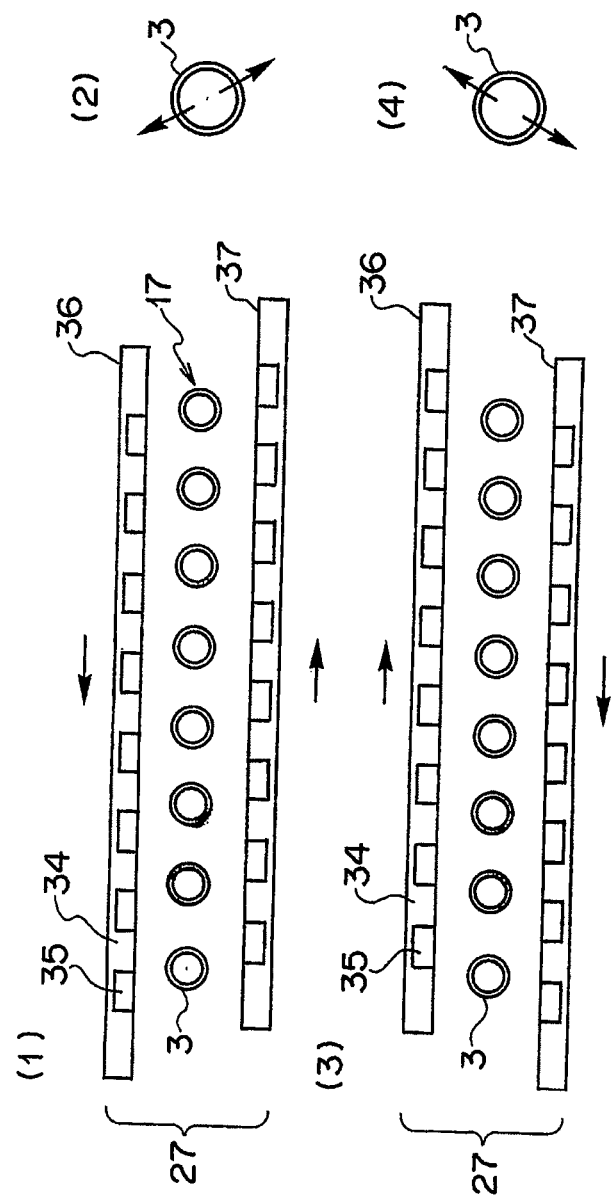
FIG. 8 is an explanatory diagram of the operation of the apparatus for introducing a biological material according to the second embodiment of the present invention.

FIG. 7 and FIG. 8 schematically show the position of the respective tips 3 of the nozzle unit 17, and the linear magnetic sources 36 and 37 in the magnetite force treatment unit 27.

FIG. 7 (1) schematically shows a case where the respective distances of the linear magnetic sources 36 and 37 are apart from the nozzle unit 17 enough to weaken the magnetic force influencing the inside of the tip 3. In this case, as show FIG. 7 (2), no arrow is shown representing the magnetic force inside each tip 3, since the magnetic force inside each tip 3 is weak.

FIG. 7 (3) shows a case where the respective linear magnetic sources 36 and 37 are made closer from the opposite sides, to the nozzle unit 17 by the transfer unit. In this case, as shown in FIG. 7 (4), each tip 3 receives the magnetic force vertically.

FIG. 7 (5) shows a case where one linear magnetic source 36 is made even closer to the nozzle unit 17 and the other linear magnetic source 37 is made further away from the nozzle unit 17. In this case, as shown in FIG. 7 (6), the magnetic force is applied in one direction only. Therefore, the magnetic supports contained in the tip 3 are attracted in one direction only, and attached to the internal wall of the tip 3, and thus separated.

FIG. 8 shows a case where the linear magnetic sources 36 and 37 are displaced by a shorter distance than the distance between the adjacent tips 3 along the horizontal line, in a state where the linear magnetic sources 36 and 37 are close to the nozzle unit 17. FIG. 8 (1) shows the state where the linear magnetic source 36 is moved to the left and the linear magnetic source 37 is moved to the right respectively by about a half of the distance between the adjacent tips 3. The magnetic force inside the respective tips 3 in this case is applied in the directions shown in FIG. 8 (2). FIGS. 8 (3) and (4) show a case where the case of the FIGS. 8 (1) and (2) is displaced in reverse directions of left and right. Similarly to the present example, the magnetic forces are applied to oppose each other with the respective tips 3 therebetween, by moving the linear magnetic sources 36 and 37. Therefore, the magnetic supports inside the tip 3 can be influenced so as to develop.

Figure 9:
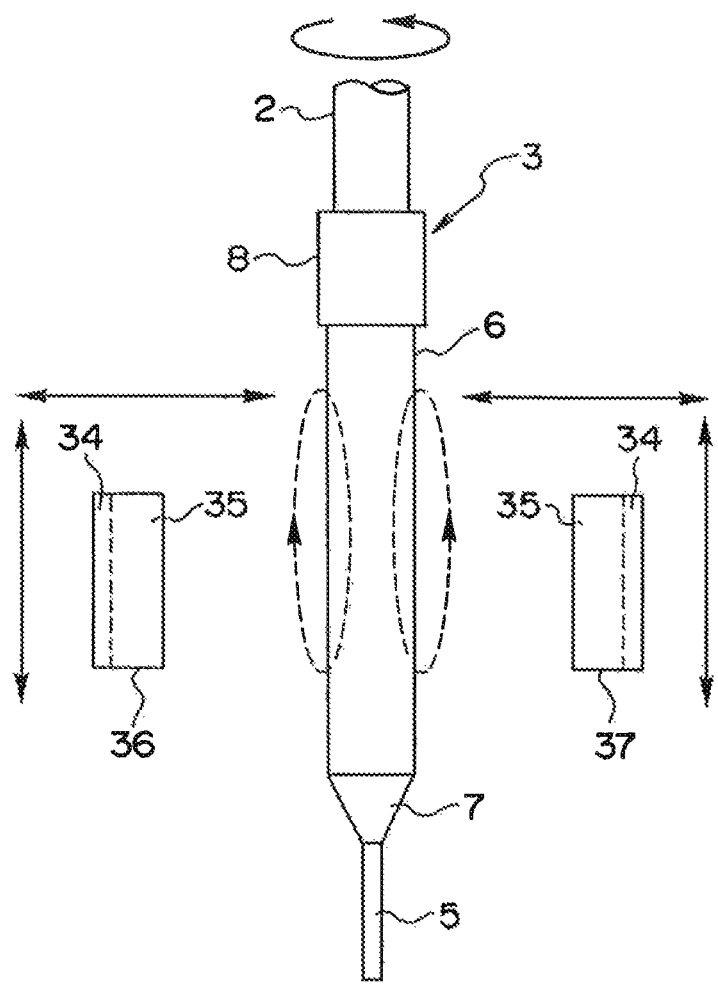
FIG. 9 is an explanatory diagram of the operation of the apparatus for introducing a biological material according to the second embodiment of the present invention.

FIG. 9 shows a state seen from the horizontal direction along the horizontal line, for when the tips 3 attached to the set of eight nozzles and linearly arranged, are moved to the magnetic force treatment unit 27 and inserted into the openings. Therefore, in FIG. 9, only one tip 3 out of eight tips is illustrated, and the magnetic force treatment unit 27 is illustrated such that the rod shaped linear magnetic sources 36 and 37 provided in parallel with the set of eight nozzles 2 on the opposite sides with the tips 3 therebetween, each have one permanent magnet block 35 out of eight provided for the supporting section 34.

The linear magnetic sources 36 and 37 are not only provided so as to be able to come closer or go away (refer to FIG. 7 and FIG. 8) with respect to the tip 3 as shown by the horizontal arrows in FIG. 9, but also so as to be movable vertically as shown by the arrows along the axial direction of the respective tips 3. Moreover, the tip 3 itself is rotatable about the axis as shown by the curved arrow.

Furthermore, it is possible to apply the magnetic force in a route as shown by the curved broken lines of the drawing, by moving the respective linear magnetic sources 36 and 37 along both of the axial direction and the close/away direction of the tip 3 at the same time. In these examples, various magnetic threes are applied to the inside of the tip 3 exclusively by moving the linear magnetic sauces 36 and 37 of the magnetic three treatment unit 27. However, it is also possible to apply the same type of magnetic force by moving the nozzle unit 17 itself. In this case, the linear magnetic sources 36 and 37 correspond to the magnetic source, and the transfer unit of the nozzle unit corresponds to the magnetic source transfer unit.

According to the present embodiment, since the magnetic force is applied to the tips being the respective packing units, from at least two directions, it is possible by the magnetic force to avoid the condition where the magnetic supports are attached to or precipitated on the wall or the bottom of the packing unit respectively. By moving the linear magnetic sources vertically and horizontally, or by rotating the respective tips, the magnetic supports can be moved relatively with respect to the host in a state where they are developed in a higher density than the other areas within the packing unit, thus increasing the number of collisions or the rate of collisions of the magnetic supports and the host, or increasing the chance of encounter, so that the introduction treatment can be performed efficiently.

In the above examples, the operation of the packing unit, the pressure adjuster, the magnetic source, the magnetic force transfer unit, the transfer unit and the like is controlled by an information processor (not shown). The information processor has: a CPU; a memory, a CDROM, a flexible disk, a DVD and the like which store various programs such as the procedure for the introduction treatment or various data on the biological material, the host, the magnetic support, the magnetic source, the environmental conditions, and the like; input devices such as a keyboard and a mouse for inputting various data such as host data, biological material data, reagent data, and the like, and instructions of various operations; output devices such as a display device and a printer which show the result of introduction, treatment status, the rate of collision, the number of collisions, or the probability of encounter (density or distribution of magnetic support or host); and a communication facility such as a modem.

Figure 10:
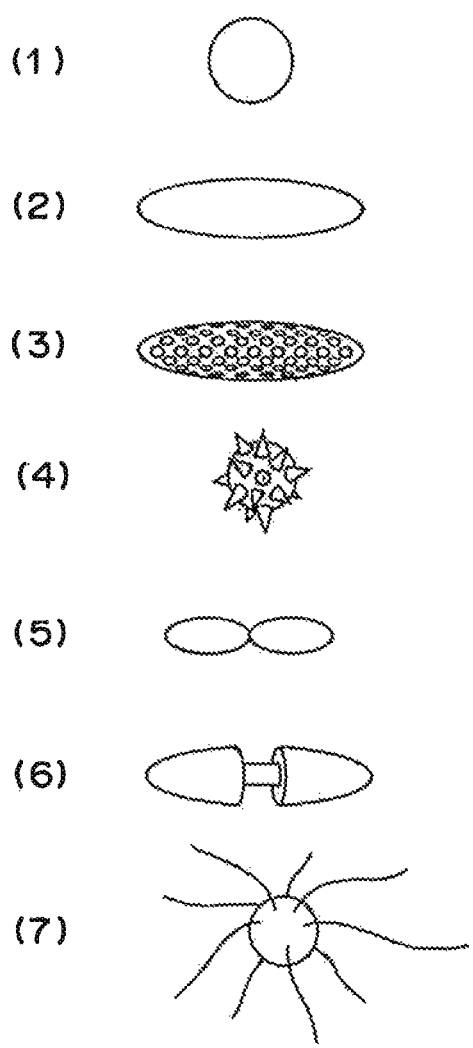
FIG. 10 is an enlarged diagram of magnetic supports according to a third embodiment of the present invention.

Next, FIG. 10 shows seven types of magnetic supports according to a third embodiment.

The first type of magnetic support shown in FIG. 10 (1) is a globular particle, having a size between 100 nm and several μm for example, which is used if the particle surface coat and the host have the good adhesive property. For the material, a magnetizable superparamagnet is used, which is made of for example, an iron hydroxide, an iron oxide hydrate, an iron oxide, a mixed iron oxide, or iron.

The second type of magnetic support shown in FIG. 10 (2) has a major axis where one axis is formed longer than the other axis, being a rotating symmetry body with respect to the major axis, and the opposite ends along the major axis are formed tapered. If it is magnetized, or formed to be magnetizable, in the major axis direction, it becomes movable by the magnetic force in the major axis direction, and thus is readily controlled. The size of the magnetic support is about between 100 nm and several μm for example, and the material is similar to that described for the first type of magnetic support. In the present example, the magnetic support has the structure for facilitating entry into the host, and is used for example in a case where there is a cell wall, or the cell membrane is silting, or a case where cell surface treatment is not performed.

The third type of magnetic support shown in FIG. 10 (3) has a porous surface, or carries other porous material. Accordingly it can reliably carry the biological material.

The fourth type of magnetic support shown in FIG. 10 (4) is globular having a large number of projections on the surface of the magnetic support itself or the material carried by the magnetic support. Accordingly, it can reliably carry the biological material between projections.

The fifth type of magnetic support shown in FIG. 10 (5) has a plurality of, for example the first to fourth types of the magnetic supports connected. The connection portion is used as the carrier. The magnetic support is readily produced and is of low price.

The sixth type of magnetic support shown in FIG. 10 (6) has a major axis longer than the other axis, being a rotating symmetry body with respect to the major axis, and the opposite ends along the major axis are formed tapered. Moreover, a carrier having an annular groove on the side face is provided. As a result, the capacity to carry the target biological material on the magnetic support can be increased. The material is similar to that of the first type of magnetic support for example.

The seventh type of magnetic support shown in FIG. 10 (7) is a complex support being, for example a globular particle-shaped object combined with filamentary supports as a carrier. It is used, for example in a case where the cell membrane is relatively weak, requiring introduction under a mild condition, in a case of a dilute fungus liquid, or in a case where handling is facilitated if the target biological materials are aggregated. The respective filamentary supports are not introduced into a host, but a load is applied to the hosts entwined with the filamentary supports by applying the magnetic force, so that the force is applied as a line, and not as a point, to reduce damage. Since this method allows treating the particle and the carrier separately, manufacture is facilitated.

If the target biological material is adhered to or combined with the magnetic support by physical adsorption or electrical interaction, they are readily separated inside the host. Moreover, the magnetic support may carry an introduction adjuvant for facilitating introduction of the magnetic support into the host. For example, when a bacterial gene is introduced, the membrane fluidity is increased by calcium chloride so as to facilitate taking in of the plasmid. In a case of an animal cell, it is protoplastized using polyethylene glycol and then introduced. Moreover, in order to increase the chance of contact with cells, cell aggregation may be promoted (crosslinking between cells by bivalent metal ions and the like) so as to perform the introduction treatment in a condition where the cells are conglomerated.

Figure 11:
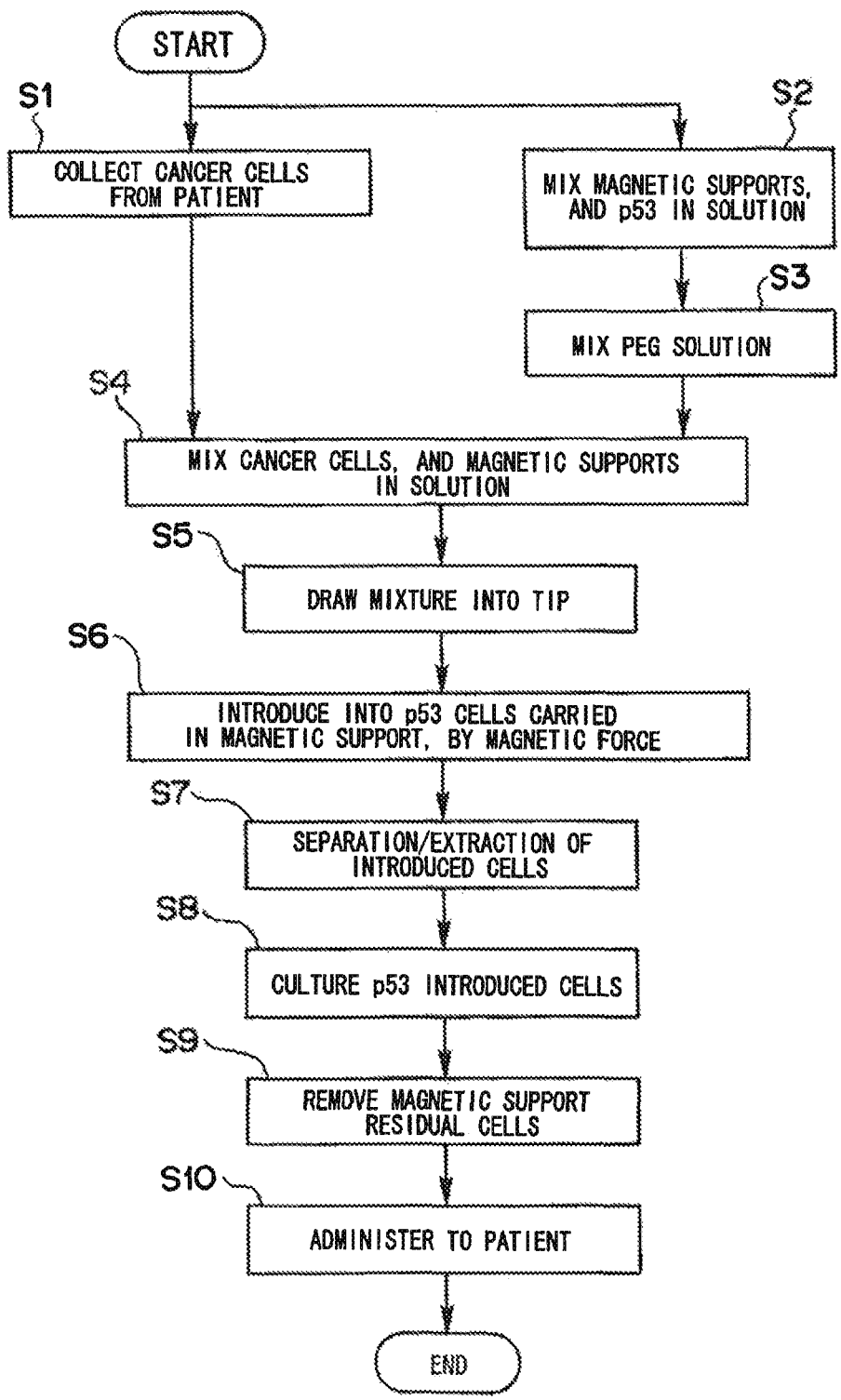
FIG. 11 is a flowchart showing an example of gene therapy according to a fourth embodiment of the present invention.

Next is a description of a gene therapy using the apparatus for introducing a biological material and the method of introducing a biological material according to a fourth embodiment, based on FIG. 11.

As shown in FIG. 11, in step S1 cancer cells collected turn a cancer patient are placed in a container. A contrast medium such as Fe (Cu) having a property of attaching to the cancer cell tissues, is administrated to the vicinity of the cancerous area by injection, the cancer cells are collected using X ray irradiation, and then put into the solution packing unit 24 of the container 25. In step S2, the magnetic supports and proteins p53 are mixed in the solution, and repeatedly drawn and discharged lightly by the nozzle unit 17, so that the magnetic support can carry the protein p53.

Here, "p53" is one type of protein which monitors the presence/absence of DNA damage in a cell at all times, and allows DNA replication only if there is no DNA damage. Moreover, when it finds an abnormality in the DNA, it inhibits transcription by a transcription factor and stops the replication of the damaged DNA, and the large number of the produced p53 repair the DNA damage rapidly. If the damage is peat at this time, it gives up repairing the cell, and gives instructions to remove the cell.

Therefore, by introducing p53 into a cancer cell, there is provided a property of stopping the replication of the cancer cell, and repairing the DNA damage rapidly.

In step S3, a PEG (polyethylene glycol) solution corresponding to the adjuvant, and the magnetic supports carrying p53 being the biological material, are mixed in a predetermined solution packing unit of the microplate 21, and lightly stirred by repeatedly drawing and discharging using the nozzle unit 17 so that the magnetic support can carry the PEG. Here, the PEG solution is to soften the cell membrane so that the magnetic support can enter readily.

In step S4, the cancer cells, and the magnetic supports carrying the p53 and the PEG are mixed in the solution to make the mixture solution in the solution packing unit of the microplate 21.

In step S5, the nozzle unit 17 is moved to the solution packing unit of the microplate 21 containing the mixture solution, and the mixture solution is drawn as far as the storage unit 6 of the tip 3.

In step S6, the nozzle unit 17 by which the mixture solution is drawn, is moved to the magnetic three treatment unit 27 while carrying the mixture solution, and the tips 3 are inserted into the openings of the magnetic three treatment unit 27.

Next, the linear magnetic sources 36 and 37 in the magnetic force treatment unit 27 are brought close to the tips 3 arranged in a linear form, and are moved by about the width of the tip 3 in parallel with the line, or are moved vertically. By so doing the magnetic supports are developed in the tip 3 and are moved within the tip 3 in the developed state, so as to increase the number of collisions or the rate of collisions of the magnetic supports and the cancer cells being the host, or increase the chance of encounter thereof thus making the magnetic support enter the cancer cell.

In step S7, after the p53 is introduced into the cancer cell by making the magnetic support enter the cancer cell, one linear magnetic source 36 in the magnetic three treatment unit 27 is brought close to the nozzle unit 17 and the other linear magnetic source 37 is taken away from the nozzle unit 17 for a predetermined distance or more. Thereby a unidirectional magnetic force is applied to the magnetic support, so as to separate the cancer cells which the magnetic supports enter, by making them attach to the inner wall of the tip 3. After discharging the residual liquid, the separated cancer cells are moved to the container 29 together with the nozzle unit 17, while being attached to the inner wall of the tip 3. By repeatedly drawing and discharging the solution in the container 29, the cells are resuspended in the solution, which is then put into the solution packing unit.

In step S8, the solution containing the separated and extracted cells where the abnormality of the DNA has been repaired by the action of the introduced p53, and into which the magnetic support has been entered, is again drawn and held by the nozzle unit 17. Then, the solution is moved to the reagent bath 18 and discharged to the media therein and the cells are cultured.

In step S9, the solution containing the repaired cells into which the p53 is introduced, is again drawn and held by the nozzle unit 17 and moved to the magnetic three treatment unit 27. One linear magnetic source 36 is brought close to the nozzle unit 17 and the other linear magnetic source 37 is taken away from it. Therefore the repaired cells which the magnetic supports have entered into and remain inside, are separated and removed by making them attach to the inner wall of the tip 3. The residual solution is discharged and put into the solution packing unit 28 of the container 29. The used tip 3 having the absorbed cells containing the magnetic supports is detached and disposed into the waste vent 30.

In step S10, the repaired cells into which the p53 obtained in this way by pure culture has been introduced, are adhered to Fe (Cu) having the property of attaching to the cancer cells, and then administrated to the diseased area of the patient by injection. When cells having p53 introduced are administrated in large amounts, the cancer cells can be removed or repaired due to the action of the p53, enabling treatment of the cancer.

Figure 12:
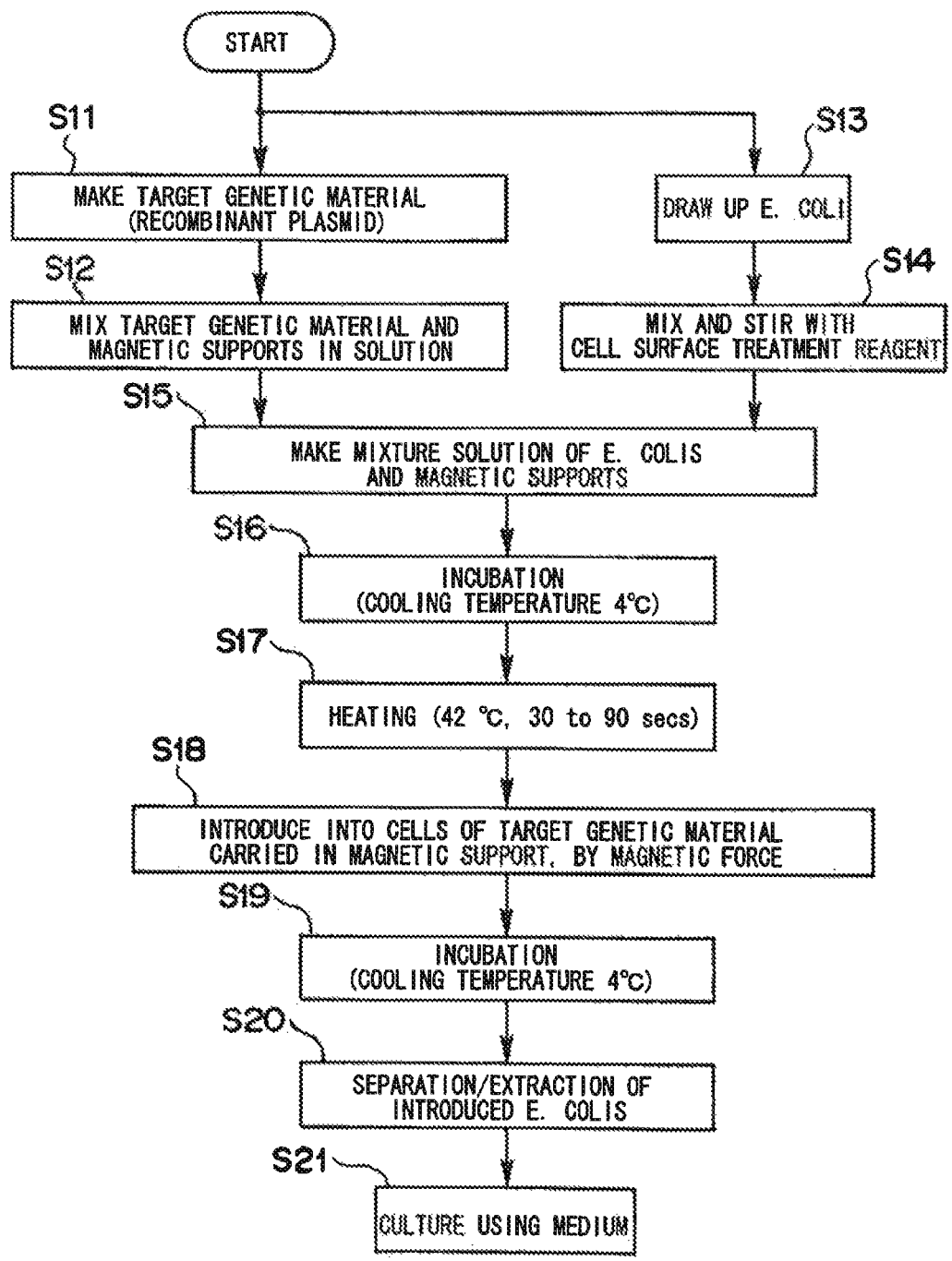
FIG. 12 is a flowchart showing an example of protein synthesis according to a fifth embodiment of the present invention.

Next is a description of a production method for a protein according to a fifth embodiment, based on FIG. 12. This method shows an example where a magnetic force is not required for separation.

In step S11, a recombinant plasmid having a target gene to produce a useful protein to be synthesized inside a cell is made. Regarding the recombinant plasmid (Pbr322), a ring-shaped plasmid is cut by adding a restriction enzyme and is made into a linear-shape, then mixed with the target gene DNA, and a DNA ligase is added thereto to make the ring-shaped recombinant plasmid.

In step S12, a large number of the recombinant plasmids are mixed with a large number of the magnetic supports in a solution, so as to make the magnetic support carry the recombinant plasmid.

On the other hand, in step S13, a solution containing *E. colis* as a host is drawn from a container in which it is contained using the nozzle unit 17. In step S14, it is moved into a container containing a surface treatment reagent as the introduction adjuvant which softens the surface of the *E. coli*, then discharged and mixed.

In step S15, a mixture solution is made by mixing *E. colis* and the magnetic supports carrying the recombinant plasmid in the solution while gently stirring, and put in the solution packing unit 20 in the microplate 21 in FIG. 4.

In step S16, the microplate 21 is cooled during incubation (cooling temperature is 4° C.) in the heated/cooled area 31, so as to recover the cells which were damaged during mixing with the reagent or during movement.

In step S17, in order ID facilitate the introduction of the plasmid as the target biological material carried by the magnetic support into the *E. coli*, heat shock is applied by heating for 30 to 90 seconds at 42° C. in the microplate 21 in the heated/cooled area 31.

In step S18, the nozzle unit 17 is moved to the microplate 21, and then to the magnetic force treatment unit 27 while drawing and holding the mixture solution, and the linear magnetic sources 36 and 37 are moved in a predetermined direction, so as to apply the magnetic three to the nozzle unit 17. As a result, in the state of being developed the mixture solution, the magnetic supports are moved relatively with respect to the host by the magnetic force, so as to increase the number of collisions or the rate of collisions, or increase the chance of encounter, making the magnetic supports enter into the *E. coli*.

In step S19, the introduction treated mixture solution is moved to the microplate 21 while being drawn into and held in the respective tips 3 of the nozzle unit 17, and discharged thereto. Then, the mixture solution is cooled down quickly to 4° C. by incubation in the heated/cooled area 31, and the cell membrane of the *E. coli* is closed to complete the introduction treatment.

In step S20, in order to separate and extract the *E. colis* into which the plasmid with the target biological material is introduced, an antibiotic is added to the mixture solution for which the introduction treatment is completed, so as to kill the *E. colis* not having the recombinant plasmid introduced, and the *E. colis* into which the plasmid is introduced are separated.

In step S21, the mixture solution containing the *E. coli* into which the plasmid is introduced, is drawn and held by the nozzle unit 17, then transferred to the medium of the reagent bath 18, and discharged to the medium.

The mixture solution discharged to the medium is cultured by incubation at 37° C. for 30 to 60 minutes and the host cells are repaired and stabilized.

The above respective embodiments have been specifically described for better understanding, and are not to be considered as limiting other embodiments. Therefore, modifications can be made without departing from the scope of the present invention. For example, in the description above, only a case where an annular magnet or two linear magnets with the tip therebetween, are used, has been described. However, the invention is not limited to this example, and for example permanent magnet blocks or electromagnets may be used in some cases.

Furthermore, in a configuration where three or more of the permanent magnet blocks or the electromagnets are arranged so as to have the same central angle as each other, around the packing unit of a circular tubular shape, a magnetic force modification unit which modifies the respective magnetic forces sequentially at a predetermined period, may be provided instead of the magnetic source transfer unit.

Alternatively, the magnetic source transfer unit may have as the magnetic source, three or more of the permanent magnet blocks or electromagnet blocks which are arranged so as to have the same central angle as each other, around the packing unit of a circular tubular shape, so that the magnetic source can be made radially closer to or apart from the packing unit or can be movable along the axial direction and the circumferential direction. Moreover, in the magnetic force treatment unit, a plurality of annular permanent magnets may be arranged instead of the linear magnetic sources. Furthermore, the linear magnetic sources may be provided for the packing unit.

Moreover, the two magnets or the magnetic poles provided so as to face each other, of the linear magnetic sources may have the same pole or opposite poles. Furthermore, it is preferable in terms of the structural stability of the apparatus, that the permanent magnet blocks arranged on the linear magnetic source are arranged to have different magnetic poles alternately, and the facing linear magnets are provided with magnetic poles different to the corresponding magnetic poles.

Only the case where the linear nozzle unit has a set of eight, has been described, however the number is not limited to "eight" and may be selected based on the number of container wells of the microplate to be used. The packing unit is not limited to the illustrated tip but has various shapes. The host and biological material are also not limited to the examples of the embodiments and have various types. Moreover, the plurality of packing units may be arranged not only in a linear form but also in a matrix form. In this case, the magnetic sources for the introduction treatment units are arranged in a matrix form corresponding to the arrangement of the packing units. Therefore, the integration can be further advanced and the introduction treatment can be further efficiently performed. The arrangement may be not only a linear form nor a matrix form, but in a curvilinear form.

Figure 13:
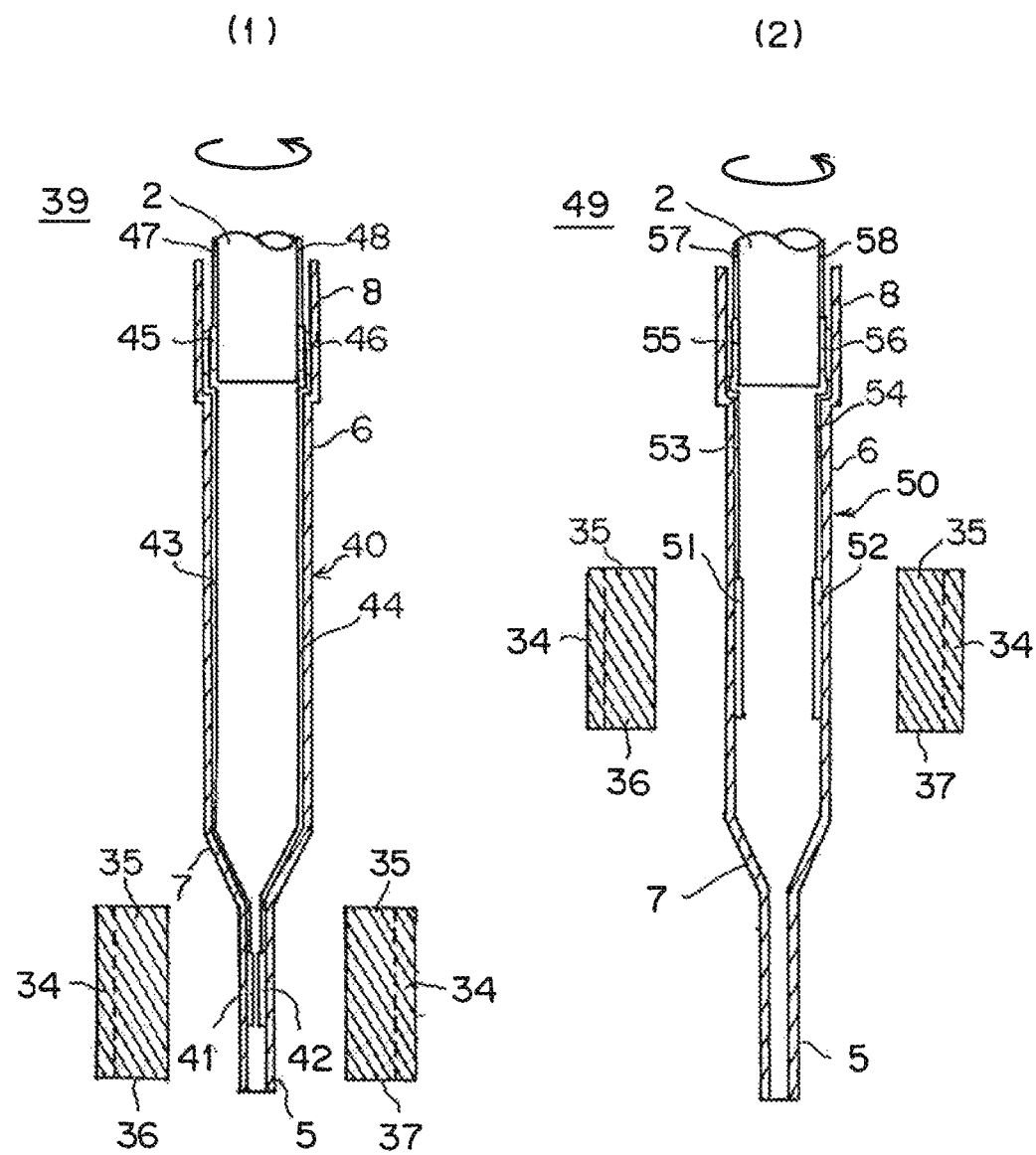
FIG. 13 is a cross-sectional view showing a main part of an apparatus for introducing a biological material according to a sixth embodiment of the present invention.
Figure 14:
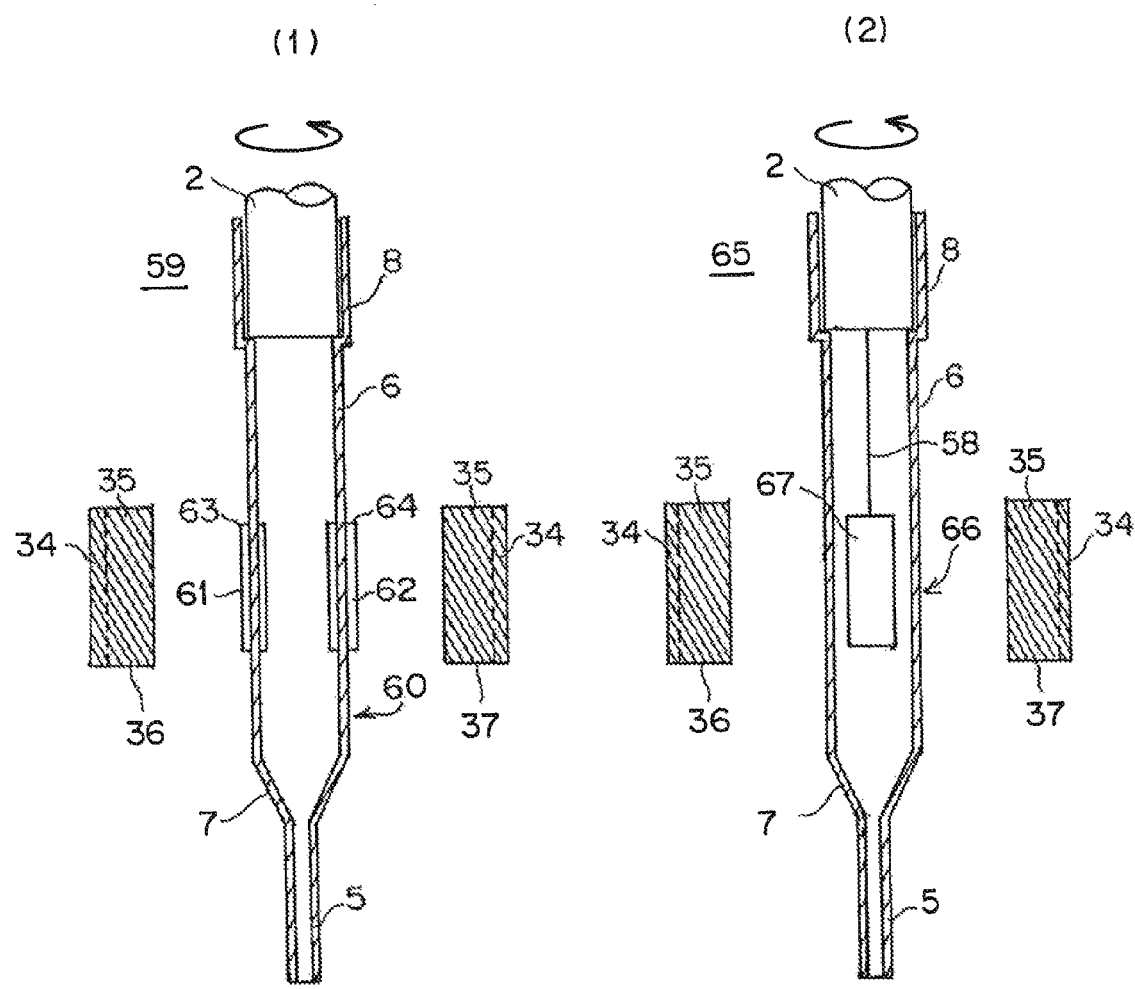
FIG. 14 is a cross-sectional view showing another example of the main part of the apparatus for introducing a biological material according to the sixth embodiment of the present invention.

Next is a description of an apparatus for introducing a biological material according to a sixth embodiment, based on FIG. 13 and FIG. 14. The same reference symbols are used for components the same to those described in the second embodiment, and the description thereof is omitted.

The apparatus for introducing a biological material according to the sixth embodiment is provided with a perforation treatment unit which perforates the cell membrane or the like, being the boundary, from the outside of the host such as the cell within the packing unit. The perforation treatment unit has a perforation force source provided at the tip corresponding to the packing unit in order to apply a perforation force to the host, and a perforation force source control unit which controls the perforation farce source. Examples of the perforation force source are described based on the drawings.

FIG. 13 (1) shows a nozzle unit 39 wherein the set of eight nozzles 2 described in the second embodiment are arranged with their respective axes vertical and in parallel with each other at intervals along the horizontal line, and tips 40 are detachably inserted into the nozzles 2 respectively. Moreover, as described in the second embodiment, the set of eight nozzles 2, and therefore the tips 40, are arranged along the horizontal line. The magnetic force treatment unit has two linear magnetic sources 36 and 37 which have rod-shaped supporting sections 34 provided on the opposite sides with the tip 3 therebetween, in parallel along the horizontal line, and eight permanent magnet blocks 35 set in positions corresponding to the respective tips 3.

In FIG. 13 (1), as the per titration force source to generate discharge pulses, a pair of facing electrodes 41 and 42 are provided on the inner wall of the small diameter liquid passage 5 of the tip 40 at a height corresponding to the linear magnetic sources 36 and 37. Conducting wires 43 and 44 reach from the respective electrodes 41 and 42 through the middle diameter unit 7 and the inner wall of the large diameter storage unit 6 to the attachment unit 8 along the axial direction. The ends of the respective conducting wires 43 and 44 are to be connected to terminals 45 and 46 which are connected with a power circuit (not shown) provided on the outer surface of the nozzle 2 via conducting wires 47 and 48, at the time of attachment. By applying a predetermined discharge pulse from the power circuit to between the pair of the electrodes 41 and 42 in a state where a magnetic force is applied by the linear magnetic sources 36 and 37, the perforation treatment is applied to the host passing through the liquid passage 5.

In FIG. 13 (2), a nozzle unit 49 is used instead of the nozzle unit 39 described in FIG. 13 (1).

In the nozzle unit 49, as the perforation force source to generate the discharge pulses, a pair of facing electrodes 51 and 52 are provided on the inner wall of the large diameter storage unit 6 of the tip 50 at a height corresponding to the linear magnetic sources 36 and 37. Conducting wires 53 and 54 are extended from the respective electrodes 51 and 52 along the inner wall of the storage unit 6 upward reaching the attachment unit 8. The ends of the respective conducting wires 53 and 54 are to be connected to terminals 55 and 56 which are connected with the power circuit (not shown) provided on the outer surface of the nozzle 2 via conducting wires 57 and 58, at the time of attachment. By applying a predetermined discharge pulse from the power circuit to between the pair of the electrodes 51 and 52, the perforation treatment is applied to the host pooled in the storage unit 6.

According to the tip 39 in FIG. 13 (1) or the tip 49 in FIG. 13 (2), it is possible to apply the voltage to the electrodes, being the perforation treatment unit, simply by attaching the tip 39 or 49 to the nozzle 2, thus facilitating the handling.

In FIG. 14 (1), a nozzle unit 59 is used instead of the nozzle units 39 and 49.

In the nozzle unit 59, as the perforation force source to generate the discharge pulses, a pair of facing electrodes 61 and 62 are provided so as to pass through the wall of the large diameter storage unit 6 of the tip 60 from the inside to the outside at a height corresponding to the linear magnetic sources 36 and 37. In order to apply the voltage to the electrodes, they may be connected to the power circuit via portions 63 and 64 exposed to the outside of the electrodes. Therefore, since it is not necessary to pass the conducting wire to inside the tip 60, which is necessary in the nozzle units 39 and 49, the internal structure can be simplified and the manufacturing cost can be reduced. Moreover, since the inside of the tip 60 is not so uneven, the flow of a fluid in the tip 60 can be smoothened.

In FIG. 14 (2), a nozzle unit 65 is used instead of the nozzle units 39, 49, and 59.

In the nozzle unit 65, as the perforation force source to generate ultrasound, an ultrasonic oscillator 67 is provided at the height corresponding to the linear magnetic sources 36 and 37. A conducting wire 58 is provided from the ultrasonic oscillator 67 along the axial direction inside the tip 66, and it is provided so that the end of the concluding wire 58 is connected to a terminal provided on the outer surface of the nozzle 2, at the time of attachment of the tip 66.

The perforation force source control unit which controls the perforation force source comprises an information processor and a program provided in the information processor. The perforation force source control unit controls the perforation force based on the properties, the amount, or the density of the host, the biological material to be inserted into the host, or the magnetic support, and on the magnetic force control unit which controls the linear magnetic sources 36 and 37. That is, regarding the perforation into the host, the intensity of the perforation force is determined by the hardness of the host, the size of the magnetic support to be entered, or the acceptable size to introduce the biological material fixed on the magnetic support when the magnetic support is attached to the host. Moreover, the generation lime, the frequency and the like of the perforation force are determined based on the amount and the density of the host or the magnetic support.

The perforation force source control unit generates the perforation force in spatial or time association with the introduction treatment, according to the properties of the host. For example, if the host is a cell, when the cell membrane is perforated, it is repaired in a short time. Therefore it is necessary to execute the introduction treatment at the same time as the perforation treatment, or to execute the perforation treatment immediately after the introduction treatment. For that reason, the introduction treatment perforation treatment are required to be executed in spatial or time association with each other.

According to the present embodiment, the biological material carried by the magnetic support can be efficiently introduced into the host by combining and controlling the electric field and the magnetic field.

Next is a description of a seventh embodiment.

In FIG. 15 (1), there we a microplate 70 having eight holes 71 into which tips can be inserted all at once using the set of eight nozzles unit 17 (or 39, 49, 59, and 65), and a separation unit 73 on which the microplate 70 is mounted and which has a plurality of permanent magnet blocks 72 arranged at positions corresponding to the bottoms of the respective holes 71. Media are contained in the respective holes of the microplate 70.

The introduction treated (or introduction treated and perforation treated) solution containing the host having the introduced magnetic support, is drawn using the set of eight nozzles unit 17, then transferred to the microplate 70 having the holes 71 containing the media, while being contained in the respective tips 3 (39, 49, 59, and 65), by moving the nozzle unit 17 itself, and then discharged into the respective holes 71 containing the media, all together.

The host is cultured by incubation in the respective holes 71 for a predetermined time at a predetermined temperature, and the first generation host contained first and having the introduced magnetic support is moved to the bottom of the respective holes 71 by the magnetic force of the permanent magnet block 72.

Then, as shown in FIG. 15 (2), by drawing only a portion which is not attached to the bottom in the respective holes 71 using the newly attached tip 74, while the linear magnetic source 36 (37) is close to the liquid passage, the pure host having the introduced and cultured biological material can be extracted.

According to the present embodiment, a pure cultured substance can be extracted efficiently and reliably with a simple apparatus.

Moreover, the abovementioned respective components, parts, units, for example, the packing unit, the container, the magnetic source, the liquid passage, the filter holder, the nozzle, the tip, the magnetic source transfer unit, the magnetic force modification unit, the permanent magnet, the electromagnet, the magnetic support, the carrier, the reagent, the host, the biological material, the magnetic force treatment unit, the introduction treatment unit, the transfer mechanism, the perforation treatment unit, the perforation force source (electrode, ultrasonic oscillator), the conducting wire, the terminal and the like may be optionally combined while appropriately modifying them if required. Particularly, the third to the eighteenth aspects of the present invention may be applied to the packing unit and the introduction treatment unit of the thirty-first aspect of the present invention, and the twentieth to the twenty-seventh aspects of the present invention may be applied to the mixing step and the introduction treatment step of the thirty-seventh aspect of the present invention.

Moreover, the arrangement may be such that, for example the unused packing unit, the liquid passage in a tip form, the liquid passage in a tip form with a filter, the filter holder, and the like are stored in a rack, making them attachable by moving the carrier of the packing unit, the nozzle of the pressure adjuster, or the liquid passage by the transfer mechanism, or that these used carrier, the liquid passage, and the like are detached and a rack to store them is provided. Therefore, the introduction treatment can be standardized and automatically performed without relying on manpower. The transfer mechanism including the packing unit containers provided outside, liquid passage, the magnetic source, and the nick, may be movably provided.

The mechanism to realize the apparatus for introducing a biological material according to the first embodiment has not been specifically described. However, it can be realized by applying the mechanism described in the biological material introduction system according to the second embodiment, to one nozzle only.

Moreover, only the case where the perforation treatment unit is applied to the set of eight nozzles unit has been described, however it is also applicable to one nozzle unit only, and the number of the nozzles in the nozzle unit is not limited to eight. The respective mechanisms, the respective parts, the forms, and the like shown in the respective embodiments described above, show only examples and are not limited by these examples. Moreover, the introduction treatment may be performed after increasing the permeability of the boundary of host in order to increase the efficiency to introduce the biological material. For that purpose, for example, the introduction may be performed after inducing the host by a divalent ion such as Ca, or after inducing the host by an organic solvent in some cases.

1, 14 . . . Apparatus for introducing a biological material
2 . . . Nozzle
3, 40, 50, 60, 66 . . . Tip
4 . . . Annular permanent magnet
5 . . . Liquid passage
6 . . . Storage unit
13 . . . Magnetic support layer
17, 39, 49, 59, 65 . . . Nozzle unit
27 . . . Magnetic force treatment unit
31, 32, 33 . . . Heated/cooled area
36, 37 . . . Linear magnetic sources
41, 42, 51, 52, 61, 62 . . . Electrodes
67 . . . Ultrasonic oscillator

The invention claimed is:
1. An apparatus for introducing a biological material comprising;
one or more packing units containing a mixture solution having a plurality of magnetic supports carrying a biological material to be introduced into a host such as a cell and having a size allowing entry into said host, and a plurality of said hosts in a solution;

a perforation treatment unit which perforates said host in the packing units with an intensity of perforation force determined by a size of the magnetic support to be entered or an acceptable size to introduce the biological material fixed on the magnetic support when the magnetic support is attached to the host;

an introduction treatment unit which moves said magnetic supports relatively with respect to said hosts in the solution by controlling a magnetic force applied to inside said packing unit from at least two directions with said packing unit therebetween so as to introduce said biological material into said hosts by encounter between the magnetic supports and the perforated hosts; and a transfer mechanism which enables relative movement between the packing unit and the introduction treatment unit, wherein said introduction treatment unit comprises: a magnetic source which can apply a magnetic force to the inside of said packing unit; and a magnetic force control unit which controls relative movement between said magnetic supports and said host by changing the relative position or the velocity between said packing unit or said mixture solution and said magnetic field itself due to said magnetic source, wherein said perforation treatment unit has: a perforation force source which is provided on the packing unit and can apply the perforation force by an electric field, or ultrasound; and a perforation force source control unit which controls said perforation force source, wherein said perforation force source control unit controls the perforation force source based on the properties, the amount, or the density of said host, said biological material, or said magnetic support, and wherein said packing unit has a liquid passage through which said mixture solution can pass and a storage unit which can store the solution, and said magnetic force control unit has a pressure adjuster which draws and discharges the solution with respect to a container provided outside of said packing unit by adjusting the pressure in said liquid passage.

2. An apparatus for introducing a biological material according to any one of claim 1, wherein said perforation force control unit or said magnetic force control unit control the introduction treatment and the perforation treatment so as to be executed in spatial or time association with each other.

3. An apparatus for introducing a biological material according to claim 1, wherein said introduction treatment unit moves said magnetic supports and said host relatively to each other in a state where a plurality of said magnetic supports in the solution contained in said packing unit are developed in solution by the magnetic force, and controls so as to move said magnetic supports.

* * * * *